US008088623B2

(12) United States Patent
Leclerque et al.

(10) Patent No.: US 8,088,623 B2
(45) Date of Patent: Jan. 3, 2012

(54) DOMINANT SELECTION MARKER FOR THE TRANSFORMATION OF FUNGI

(75) Inventors: Andreas Leclerque, Heidelberg (DE); Hong Wan, Solna (SE)

(73) Assignee: Andreas Leclerque, Heidelberg (DE)

( * ) Notice: Subject to any disclaimer, the term of this patent is extended or adjusted under 35 U.S.C. 154(b) by 492 days.

(21) Appl. No.: 10/546,849

(22) PCT Filed: Feb. 9, 2004

(86) PCT No.: PCT/DE2004/000211
§ 371 (c)(1),
(2), (4) Date: Feb. 14, 2007

(87) PCT Pub. No.: WO2004/076672
PCT Pub. Date: Sep. 10, 2004

(65) Prior Publication Data
US 2007/0178594 A1 Aug. 2, 2007

(30) Foreign Application Priority Data
Feb. 24, 2003 (DE) .................. 103 07 969

(51) Int. Cl.
C12N 15/63 (2006.01)
C07H 21/04 (2006.01)
(52) U.S. Cl. ....................... 435/471; 536/23.1
(58) Field of Classification Search .......... None
See application file for complete search history.

(56) References Cited

U.S. PATENT DOCUMENTS 5,258,302 A * 11/1993 Vedvick et al. .......... 435/254.23
5,767,362 A   6/1998 Best

FOREIGN PATENT DOCUMENTS
EP      1 241 262    9/2002
WO    WO 99/32635   7/1999

OTHER PUBLICATIONS

Nikolskaya T et al: "Herbicide sensitivity determinant of wheat plastid acetyl-CoA carboxylase is located in a 400-amino acid fragment of the carboxyltransferase domain" Proceedings of the National Academy of Sciences of the U.S., vol. 96, No. 25 Dec. 7, 1999, pp. 14647-14651.
Madoka Y et al: "Enhancement of the plastidic acetyl-CoA carboxylase level using the tobacco plastid transformation", Photosynthesis Research, vol. 69, No. 1-3, 2001, p. 268.
Zagnitko O et al: "An isoleucine/leucine residue in the carboxyltransferase domain of acetyl-CoA carbosylase is critical for interaction with aryloxyphenoxypropionate and cyclohexanedione inhibitors", Proceedings of the National Academy of Sciences of the U.S., vol. 98, No. 12, Jun. 5, 2001, pp. 6617-6622.
Vahlensieck H F et al: "Identification of the Yeast ACC1 Gene Product (Acetyl-CoA Carboxylase) as the target of the polyketide fungicide soraphen A", Current Genetics, Feb. 1, 1994, pp. 95-100.
Cronan John E Jr. et al: "Multi-subunit acetyl-CoA carboxylases", Progress in Lipid Research, vol. 41 No. 5, Sep. 2002, pp. 407-435.
Gerth K et al: The Soraphens: A Family of Novel Antifungal Compounds from Sorangium Cellulosum (Myxobacteria), Journal of Antibiotics, Jan. 1, 1994, pp. 23-31.

* cited by examiner

Primary Examiner — Nancy Vogel
(74) Attorney, Agent, or Firm — Joyce von Natmer; Pequignot + Myers LLC

(57) ABSTRACT

The invention relates to a new expression vector for the transformation of eukaryotic cells, in particular fungal cells, or eukaryotic cell organelles as well as to a method for the transformation of eukaryotes, in particular fungi, or eukaryotic cell organelles employing these expression vector. The expression vector comprises at least one acc gene encoding at least one subunit of a MS-type acetyl-CoA carboxylase (MS-ACC), placed under the control of eukaryotic expression signals, and is a suitable selection marker for the transformation of eukaryotic cells, in particular fungal cells, or eukaryotic cell organelles to resistance to an inhibitor of MF-type acetyl-CoA carboxylases. The method involves the application of one or several acc genes encoding one or several subunits of a MS-type acetyl-CoA carboxylase (MS-ACC), as selection marker for the transformation of eukaryotic cells, in particular fungal cells, or eukaryotic cell organelles to resistance to an inhibitor of MF-type acetyl-CoA carboxylases, whereby the respective gene or genes is/are part of said expression vector and is/are under the control of eukaryotic expression signals.

12 Claims, 5 Drawing Sheets

Figure 1:
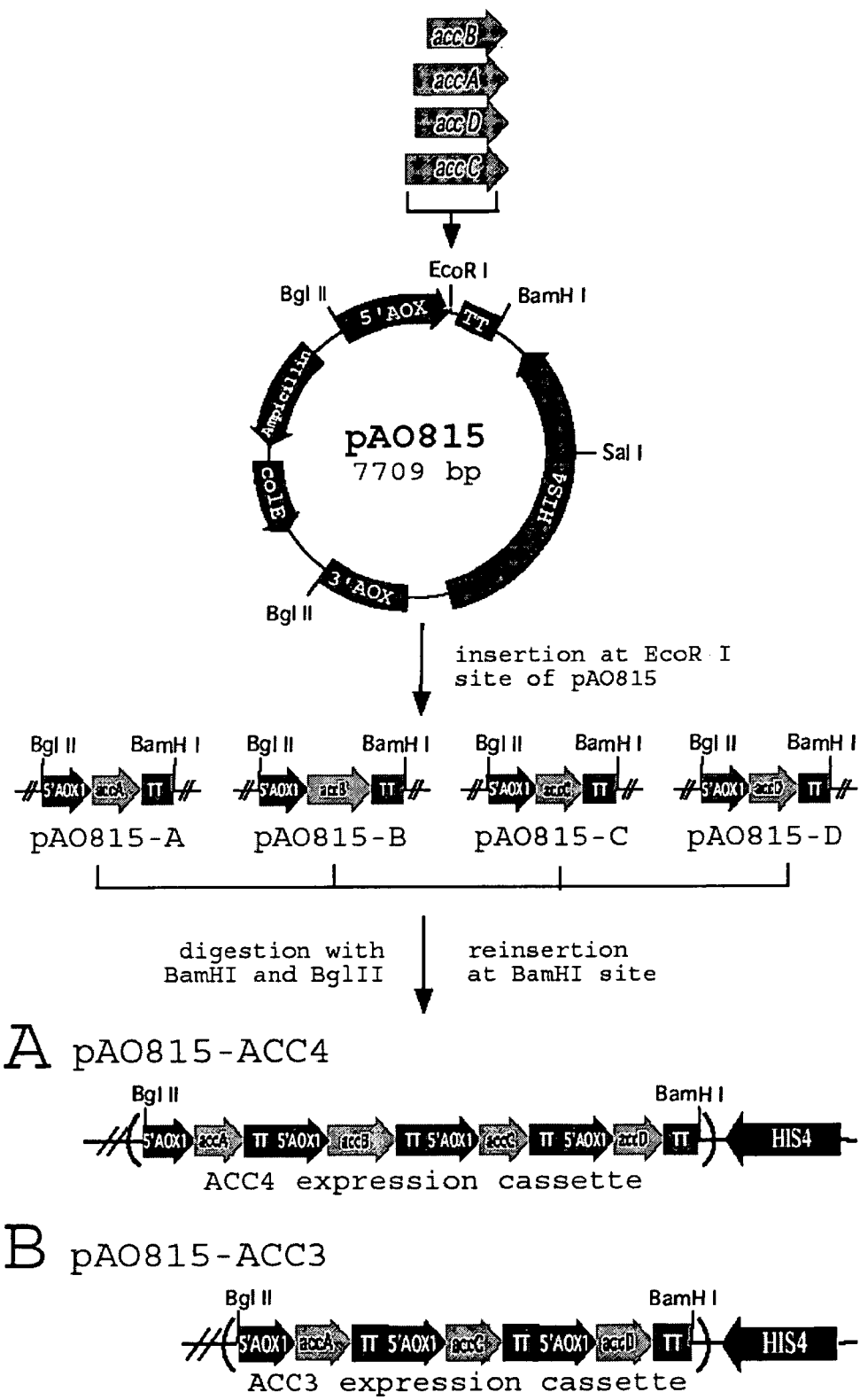

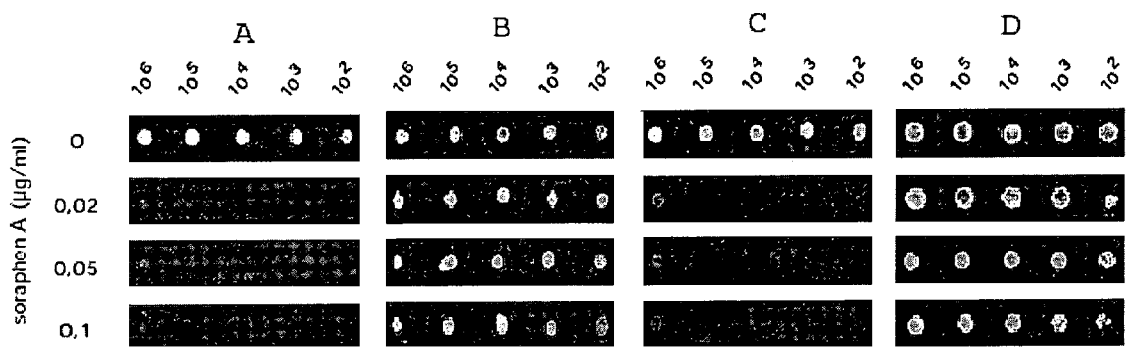
*FIG. 2A-D*

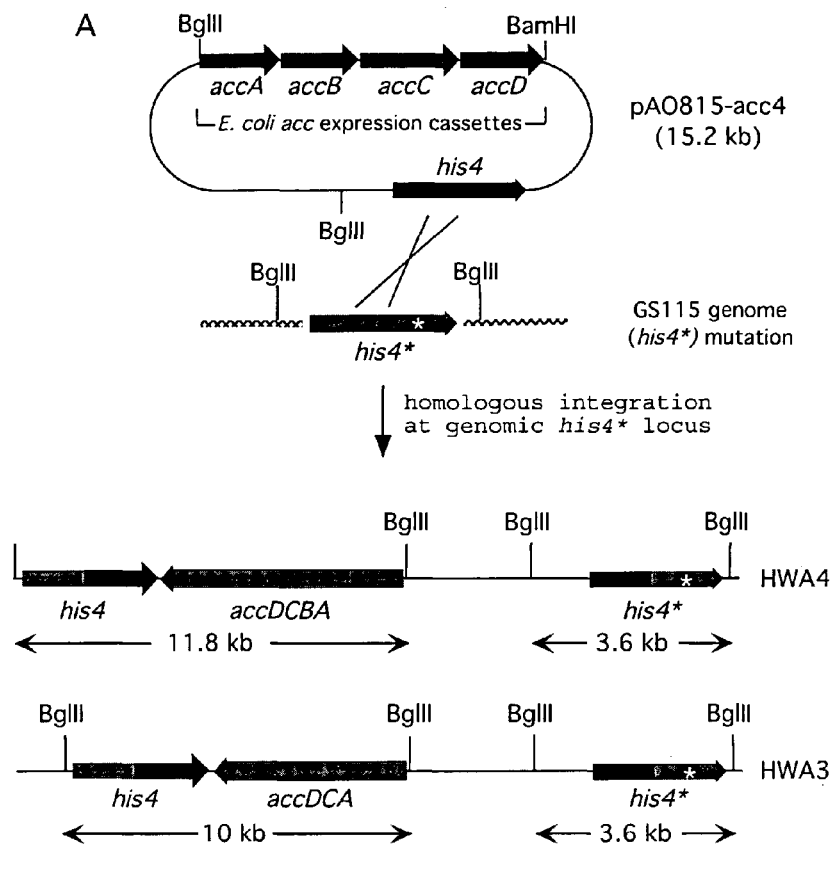
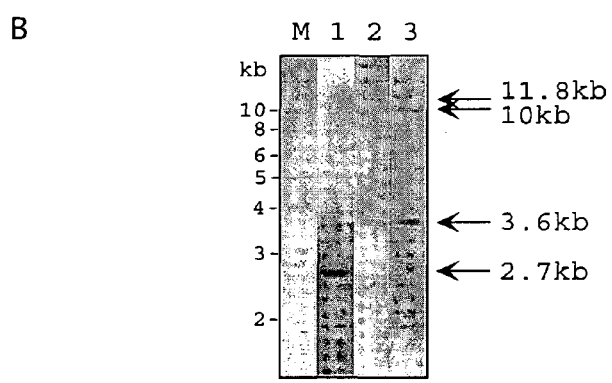
FIGURE 3 A&B

DOMINANT SELECTION MARKER FOR THE TRANSFORMATION OF FUNGI

The present invention relates to a novel expression vector for the transformation of eukaryotic cells, in particular fungal cells, or eukaryotic cell organelles as well as to a method for the transformation of eukaryotes, in particular fungi, or eukaryotic cell organelles employing this expression vector.

The functional analysis of fungal genes, and in particular the successive transformation of the same organism, relies on efficiently working selection markers. However, there are considerable limitations to a widespread application of many of the existing selection markers employed to date in the transformation of fungi. There is, therefore, still a need of efficiently working dominant selection markers to be used in the transformation of fungi.

In particular, potential selection markers are genes the expression of which confers to the transformed organism a resistance to a certain fungicide or antimycotic rendering possible the positive identification and isolation of transformants.

Soraphen A, a macrocyclic polyketide produced by strain So ce26 of the cellulolytic myxobacterium Sorangium cellulosum, is a known fungicide or antimycotic, respectively. Soraphen A is a strong inhibitor (MIC values below 1 ug/ml) of the growth of numerous filamentous fungi and yeasts, whereas bacteria or prokaryotes, respectively, are generally not sensitive to Soraphen (2). Further evidence shows that Soraphen A inhibits the acetyl-CoA carboxylase (ACC) activity of yeast and filamentous fungi (5), and this inhibition is believed to be the basis of the growth-inhibiting effect of Soraphen A upon these organisms.

The enzyme acetyl-CoA carboxylase (ACC) generates malonyl-CoA from acetyl-CoA and thereby catalyses the "committed step" of fatty acid synthesis in both prokaryotes and eukaryotes. The catalyzed reaction consists of two consecutive partial reactions, the carboxylation of the prosthetic group biotin and the subsequent transfer of the carboxyl moiety from biotin to acetyl-CoA.

ACC comprises three functional domains: a biotin-carboxylase domaine (BC) catalyzing the carboxylation of the covalent bound prosthetic group biotin with bicarbonate, a carboxyl transferase (CT) domain generating Malonyl-CoA by transferring the carboxyl moiety from biotin to acetyl-CoA, and a third domain, the so-called "biotin carboxyl carrier protein" (BCCP) that carries the essential prosthetic group.

With respect to subunit structure and organization, two classes of ACC can be distinguished: (I.) the "multi subunit" or MS-type (MS-ACC), characterized in that a functional ACC complex consists of several (mostly four) subunits encoded by different genes, and (II.) the "multifunctional" or MF-type ACC (MF-ACC), characterized in that it is made up of one single polypeptide chain comprising the three functional domains.

MS-type acetyl-CoA carboxylases (MS-ACCs) are typically found in bacteria and in the chloroplasts of dicotyledonous plants, whereas MF-type acetyl-CoA carboxylases (MF-ACCs) are known from animals, fungi, and the plant cytosol. Furthermore, the plastidic ACC of monocotyledonous plants is generally organized as an MF-type enzyme.

MF-ACC encoding genes are known from numerous plants, from the yeast S. cerevisiae (1) as well as from several filamentous fungi.

The MF-ACC paradigmatic for fungi and eukaryotes consists of a single multifunctional polypeptide encoded by a single gene which is generally referred to as acc1. In contrast, the MS-type ACC typical for prokaryotes (e.g. the bacterium E. coli) is made up of four distinct polypeptide subunits carrying the BC-, CT-, and BCCT-functions and forming the functional ACC complex. The complete set of genes coding for that MS-ACC in E. coli has been cloned previously (3, 4). The four bacterial ACC-subunits are encoded by the genes accA (SEQ ID NO: 1) (CTalpha), accB (SEQ ID NO: 2) (BCCP), accC (SEQ ID NO: 3) (BC), and accD (SEQ ID NO: 4) (CT beta). The polypeptides encoded by accA and accD together constitute the carboxyl transferase activity, while the accC gene encoded protein AccC represents the biotin carboxylase subunit. After post-translational biotinylation, the biotin carboxyl carrier protein (BCCP) encoded by the accB gene carries the prosthetic group. The four procaryotic acc genes are localized in a disperse manner throughout the E. coli genome: while accA and accD form monocistronic transcripts, accB and accC are co-transcribed from the same operon (3, 4).

Studies on the Soraphen A resistance formation in yeast revealed that the eukaryotic MF-ACC is a target of Soraphen: on the basis of the mapping of spontaneous Soraphen A resistance mutations to the acc1 gene of Saccharomyces cerevisiae the MF-ACC has been identified as target of Soraphen A (5). Soraphen resistance conferring mutations of the S. cerevisiae MF-ACC, and in particular of its biotin carboxylase domain, are object of EP 0 658 622 A2.

Furthermore, Soraphen A has been shown to inhibit in vitro the activities of MF-ACC purified from the phytopathogenic basidiomycete Ustilago maydis and from rat liver.

The activity of MF-type ACC enzymes is impaired, too, by a number of further chemical compounds, i.e. MF-ACCs represent the or at least a target for other chemicals:

The so-called "fop" and "dim" herbicides, i.e. aryloxy phenoxy propionate and cyclohexanedion compounds used for the control of grass weeds, are strong inhibitors of the plastidic MF-ACC of monocotyledonous plants.

Furthermore, fop herbicides inhibits growth of Toxoplasma gondii, presumably due to an aryloxy phenoxy propionate sensitivity of the apicoplastidic MF-ACC.

With respect to the inhibition of MF-ACCs by aryloxy phenoxy propionates and cyclohexanediones, resistance conferring mutations have been identified within the carboxytransferase domain of the respective acc-genes, e.g. in the case of the plastidic MF-ACCs from several plants (maize, wheat, lolium) and the apicoplastidic MF-ACC from T. gondii. The resistance conferring potential of said mutations has been studied by transformation of the mutated genes into a fatty acid auxotrophic ACC null mutant of the yeast Saccharomyces cerevisiae (complementation test) under selection for fatty acid prototrophy.

It is the purpose of the present invention to make available new selection markers suitable for being incorporated into vectors for the transformation of fungal and yeast cells.

On the one hand (A), this purpose is fulfilled by providing an expression vector (an expression cassette or a marker gene cassette) for the transformation of eukaryotic cells, in particular fungal cells, or eukaryotic cell organelles characterized by (1) containing (comprising) at least one acc gene that encodes at least one subunit of a MS-type acetyl-CoA carboxylase (MS-ACC) and is placed under the control of eukaryotic expression signals (in particular of an eukaryotic promotor), and by (2) being suitable as selection marker for the transformation of eukaryotes, in particular fungi, or eukaryotic cell organelles, said selection marker generating a resistance to an inhibitor of MF-type acetyl-CoA carboxylases. In other words: genes encoding subunits of a MS-type acetyl-CoA carboxylase are employed in said expression cassette (marker gene cassette) to transform eukaryotes or eukaryotic cell organelles to resistance to MF-type acetyl-CoA carboxylase inhibitors.

One the other hand (B), this purpose is fulfilled by the application of one or several acc genes encoding one or several subunits of a MS-type acetyl-CoA carboxylase (MS-ACC), as selection marker for the transformation of eukaryotes, in particular fungi, or eukaryotic cell organelles to resistance to a MF-type acetyl-CoA carboxylase inhibitor, whereby the respective gene or genes is/are part of an expression vector and is/are under the control of eukaryotic expression signals.

The acc gene or genes are either of prokaryotic origin, i.e. naturally present in the genome of prokaryotes, or is/are produced from or with the help of prokaryotic structures, e.g. from or with the help of the genome of mitochondria or plastids.

Particularly suitable acc genes encoding the subunits of the MS-type acetyl-CoA carboxylase of bacteria are the prokaryotic acc-genes, in particular the genes accA, accB, accC, and accD known for *E. coli* and numerous other bacteria.

A particularly suitable eukaryotic expression signal is the methanol-inducible aox1 promotor from yeast cells.

Each single acc gene can be part of a separate expression vector (expression cassettes).

Preferably, two or more of said aox1::acc expression cassettes carrying a separate gene are combined in a tandem configuration within the same vector, so that the vector concerned contains two or more prokaryotic acc genes.

In a particularly preferred embodiment the vector contains all four of the acc prokaryotic genes accA, accB, accC, and accD from *E. coli* in a tandem configuration.

Said expression vector particularly can have the nucleotide sequence referred to by SEQ ID NO:6.

In a further particularly preferred embodiment the vector only contains the three prokaryotic acc genes accA, accC, and accD.

Said expression vector particularly can have the nucleotide sequence referred to by SEQ ID NO:5.

The present invention relates to the surprising finding that the MS-ACC from prokaryotes or prokaryotic structures as mitochondria and plastids is insensitive to inhibitors of the eukaryotic MF-ACC, in particular to inhibitors of the MF-ACC from fungi. In other words: it has been surprisingly observed that by the expression of genes encoding subunits of a MS-type acetyl-CoA carboxylase in an eukaryote, in particular in a fungus and preferably in the yeast *Pichia pastoris*, a MS-ACC complex is formed that is functional in vivo and obviously does not represent a target of inhibitors of the eukaryotic MF-type ACC, in particular not a target of the myxobacterial fungicide Soraphen A.

In the course of the present invention the first transformation of a eukaryote to resistance to an inhibitor of MF-type acetyl-CoA carboxylases making use of genes encoding subunits of a MS-type acetyl-CoA carboxylase was successfully carried out.

It has been shown for the first time that the formation of a functional MS-ACC complex in the eukaryotic cytosol can be achieved by the integration of a complete set of prokaryotic acc genes into the genome of yeast cells.

The polyketide compound Soraphen, in particular Soraphen A, has proven to be a particularly suitable MF-ACC inhibitor. A pronounced sensitivity to Soraphen A is the rule among fungi, and the experiments leading to the present invention have shown that in contrast to eukaryotic MF-ACC and in particular to MF-ACC in fungi, prokaryotic MS-ACC, i.e. MM-ACC from prokaryotes (in particular bacteria) or from prokaryotic structures (in particular plastids or mitochondria),—in particular the MS-ACC from *E. coli*—, are insensitive to inhibition by the polyketide compound Soraphen A and are therefore obviously no target of the fungicide Soraphen A.

The yeast *Pichia pastoris* is a Soraphen-sensitive eukaryote particularly suitable for the implementation of the present invention.

The invention will be illustrated by reference to the following examples and figures, wherein the figures show FIG. 1: Schematic representation of the construction of plasmid pAO815-ACC4 (SEQ ID NO: 6) containing all four prokaryotic acc-genes (accA, accB, accC, and accD from *E. coli*), and of plasmid pAO815-ACC3 (SEQ ID NO: 5) containing only the *E. coli* genes accA, accC, and accD and with the accB gene lacking.

FIG. 2A-2D: Growth of *Pichia pastoris* strains on MM plates containing different concentrations of Soraphen A (0-0.1 μg/ml). FIG. 2A recipient strain GS115. FIG. 2B transformant HWA4. FIG. 2C transformant HWA3. FIG. 2D transformant HWA3p. Plates were locally inoculated with $10^6$ to $10^2$ cells and incubated for six days at 30° C.

FIG. 3A-3B: FIG. 3A Schematic representation of the integration of a copy of the vectors pAO815-ACC4 and pAO815-ACC3 by single crossover insertion at the his4 locus of the recipient strain *P. pastoris* GS115. The predicted size of restriction fragments is indicated below the vector map. FIG. 3B Southern blot analysis of different *P. pastoris* strains. M, DNA size standard (1 kb ladder); lane 1, DNA from strain GS115; lane 2, DNA from transformant HWA4; lane 3, DNA from transformant HWA3. DNA has been digested with BglII and hybridized with a his4-specific probe. The unexpected 2.4 kb band was observed only when an additional hybridization probe against the DNA size standard was present.

FIG. 4: Schematic representation of the homologous integration of one or several copies of plasmid pPIC3.5K-BCCP in one of both his4 loci of the Soraphen sensitive *P. pastoris* strain HWA3:

Ls=single integration into the left his4 locus; Lm=multiple integration into the left his4 locus; Rs=single integration into the right his4 locus; Rm=multiple integration into the right his4 locus. The predicted size of restriction fragments is indicated below the vector map.

FIG. 5: Southern blot analysis of different *P. pastoris* strains:

lanes 1-2=DNA from Soraphen A sensitive transformants
lane 3=DNA size standard
lane 4=DNA from the fully Soraphen resistant transformant HWA3p
lanes 5-6=DNA from transformants of intermediate Soraphen A resistance
DNA was digested with BglII and hybridized with a his4-specific probe. The unexpected 2.4 kb band was observed only when an additional hybridization probe against the DNA size standard was present.

Sequence protocols SEQ ID NO.: 1 to NO.: 15 refer to the following peptides, proteins and/or nucleic acids:

NO 1: accA gene from *E. coli* (CTalpha)
NO 2: accB gene from *E. coli* (BCCP)
NO 3: accC gene from *E. coli* (BC)
NO 4: accD gene from *E. coli* (CTbeta)
NO 5: invention-related vector pAO815-ACC3 containing the acc genes accA, accC, and accD
NO 6: invention-related vector pAO815-ACC4 containing the acc genes accA, accB, accC, and accD
NO 7: vector pPIC3.5K-BCCP
NO 8: accA forward primer NO 9: accA reverse primer
NO 10: accB forward primer
NO 11: accB reverse primer
NO 12: accC forward primer
NO 13: accC reverse primer
NO 14: accD forward primer
NO 15: accD reverse primer

EXAMPLE 1

Generation of Resistance to Soraphen A in the Yeast *Pichia pastoris* by transformation Employing the Four acc Genes (accA-accD) from *E. coli*

By transforming the yeast *Pichia pastoris* with the help of the four acc genes (accA-accD) from *E. coli* a resistance to Soraphen A was generated in that organism. The transformation was carried out using the Multi Copy *Pichia* Expression System (Invitrogen).

(A) Materials and Methods

Strains and Growth Conditions

The his4 negative *Pichia pastoris* strain GS115 (Invitrogen) was used as recipient for developing the desired selection marker. *P. pastoris* cells were cultivated at 30° C. in YPD medium (1% yeast extract, 2% peptone, 2% dextrose).

For selection of transformants, RDB agar (1 M sorbitol, 2% dextrose, 1.34% yeast nitrogen base, 0.00004% biotin, 0.005% amino acids, 2% agar), YPD-G418 agar (0.25mg G418/ml YPD medium), and MM-Soraphen-lates (1.34% yeast nitrogen base, 0.00004% biotin, 2% methanol, and 0.02 µg/ml Soraphen A) were used, respectively.

*E. coli* strains XL1-blue (MRF') and ABLE K (Stratagene) were used for plasmid propagation.

Determination of the Soraphen A Sensitivity of *Pichia pastoris*

Two methods were used to determine the concentration of Soraphen A inhibitory to the growth of *P. pastoris* GS115. On the one hand MM plates containing 0 to 0.1 µg/ml Soraphen A were locally inoculated with $10^6$ to $10^2$ cells. On the other hand 5000 cells were streaked onto such plates. Inokulations were incubated in duplicate at 30° C. for six days; 100 µl of 100% methanol was added daily to the lid of the inverted plates.

Plasmid Construction

For the construction of plasmids pAO815-ACC3 and -ACC4, the four acc genes were separately PCR-amplified from plasmids using Deep Vent DNA polymerase (New England Biolabs). After digestion with EcoRI (accA, B, C) and MfeI (accD), repectively, the four acc genes were subcloned into the EcoRI-restriction site of the *Pichia*-vector pAO815 (Invitrogen, CH Groningen, The Netherlands). The genes accB and accC that are co-transcribed in *E. coli*. were separated for that purpose.

The following primers were used:

accA forward:
(SEQ ID NO 8)
5'-GACTAATACG AATTCACCAT GAGTCTGAAT TTCCTTG accA reverse:
(SEQ ID NO 9)
5'-CAGAACTTTG AATTCTTACG CGTAACCGTA GCTC accB forward:
(SEQ ID NO 10)
5'-AGAGTACGGG AATTCACCAT GGATATTCGT AAGATT accB reverse:
(SEQ ID NO 11)
5'- AGCATGTTCG AATTCTTACT CGATGACGAC CAG accC forward:
(SEQ ID NO 12)
5'-TCGAGTAACG AATTCACCAT GCTGGATAAAA TTGTT accC reverse:
(SEQ ID NO 13)
5'-GACGCTTTAG AATTCTTATT TTTCCTGAAG ACC accD forward:
(SEQ ID NO 14)
5'-CAGACAGAAC AATTGACCAT GAGCTGGATT GAACG accD reverse:
(SEQ ID NO 15)
5'-CCCTGCCCTC AATTGTTATC AGGCCTCAGG TTC All forward primers contained substitutions, which changed the three nucleotides immediately preceding the start codon into ACC, the yeast consensus for optimal translational initiation.

The four expression vectors or aoxI.::acc expression cassettes, respectively, obtained by in this manner were designated pAO815-A, pAO815-B, pAO815-C, and pAO815-D, respectively (see FIG. 1). In the cited constructs each of the bacterial acc genes is placed under the control of the methanol-inducible aox1 promoter of yeast.

During subsequent subcloning reaktions the obtained aox1::acc expression cassettes were combined in a tandem orientation in the same vector (see construction pattern, FIG. 1); in this way the plasmid pAO815-ACC4 (SEQ ID NO: 6) containing the complete set of prokaryotic acc genes in, and the plasmid pAO815-ACC3 (SEQ ID NO: 5) which lacks only the accB gene, were formed. The proceeding in detail was the following:

Based on pAO815-A, -B, -C, and -D, plasmids pAO815-ACC3 and -ACC4 were constructed according to the "in vitro multimerization protocol" of the Multi Copy *Pichia* Expression System (Invitrogen). The aox1::acc expression cassettes were excised from each of the described plasmids by digestion with Bgl II and BamH I and inserted into the BamH I site of another plasmid. By combinatorial repetition of this process all four acc-cassettes were combined in pAO815-ACC4 whereas in pAO815-ACC3 only accA, accC and accD were obtained.

Furthermore, for generating plasmid pPIC3.5K-BCCP the accB expression cassette from pAO815-B was subcloned into the *Pichia* vector pPIC3.5K (Invitrogen), which in addition to the elements present in pAO815 contains a G418 resistance cassette.

Besides that both plasmids pAO815-ACC4 (SEQ ID NO: 6) and pAO815-ACC3 (SEQ ID NO: 5) contain the complete his4 gene from *Pichia*. Therefore, transformation of the His4-defective *Pichia* strain GS115 with these constructs allows a selection for histidine prototrophy. In addition homologous integrations into the (point-mutated) genomic his4 locus are the highly favored recombination event.

Transformation of *Pichia pastoris*

Transformation of spheroplasts was carried out with 10 µg of Sal I-linearized plasmid pAO815-ACC3 or pAO815-ACC4 following the manufacturer's instructions. Transformants were selected on RDB plates and in a second selection round the obtained histidine prototroph clones were tested for Soraphen A sensitivity on MM plates containing Soraphen A (0-0.1 µg/ml).

For transformation by electroporation, 3-12 µg of Sal I-linearized plasmid pPIC3.5K-BCCP was mixed with the competent cells and pulsed in 0.1 cm electroporation cuvettes at 1.5 kV, 25 µF, and 200Ω using a Gene Pulser (Bio-Rad). Immediately after the pulse, 1 ml of 1 M sorbitol was added to the cuvette and the cells were incubated for regeneration for 1 hour at room temperature. The cell suspension was aliquoted into two sterile Eppendorf tubes, 0.5 ml of YPD medium or MM medium was added, respectively, and the cells were incubated for 3 more hours at room temperature thereby being shaken. 50-200 µl of the aliquots in YPD were spread on YPD-G418 plates to select G418 resistant transformants, whereas aliquots in MM medium were spread on MM-agar containing 0.02 µg/ml Soraphen A.

Double Selection for Soraphen A Resistance

Histidine prototrophic or G418 resistant transformants were grown overnight in 20 ml MM medium. The cells were harvested by centrifugation and spotted onto MM plates containing different concentrations of Soraphen A (0-0.1 µg/ml). Duplicated plates were incubated at 30° C. for six days under daily addition of methanol.

Southern Blotting

Chromosomal DNA was isolated from *P. pastoris* according to standard protocols. Equal amounts of DNA were digested with BglII, separated by electrophoresis on a 0.8% agarose gel and transferred to a nylon membrane. A hybridization probe was amplified by PCR from the his4 gene present in plasmid pAO815. Specific hybridization signals were detected using the biotin-luminescent detection system (Roche) following the manufacturer's instructions.

(B) Results

Assessment of the Soraphen A Sensitivity of the *Pichia pastoris* Recipient Strain GS115

In previous studies of the growth inhibiting effect on fungi of Soraphen A variations of the MIC values ranging from 0.03 µg/ml for *Mucor hiemalis* to 4 µg/ml for *Ustilago zeae* were determined (2). A sufficient Soraphen A sensitivity of the recipient strain is a prerequisite for the application of this compound for the selection of transformants. For assessment of the Soraphen A sensitivity of the histidine auxotrophic *Pichia pastoris* strain GS115 point inoculation as well as surface inoculation were employed with several concentrations. With both methods Soraphen A concentrations as low as 0.02 µg/ml led to a complete inhibition of the growth of *P. pastoris* GS115 (FIG. 2A).

Compared to other fungi and yeast there is therefor a high sensitivity to Soraphen. For carrying out transformation experiments with direct selection for Soraphen resistance a concentration of 0.02 µg/ml Soraphen A was chosen.

Assessment of Soraphen A Resistance of the Transformed Host Strain *Pichia pastoris* GS115

To address whether expression in *P. pastoris* will result in transformation to Soraphen resistance, strain GS115 was transformed with plasmid pAO815-ACC4. Plasmid pAO815-ACC4 contains all four acc genes (accA, accB, accC and accD). Transformants were selected for histidine prototrophy.

In five randomly selected clones, the integration of the acc expression cassettes (containing all four acc genes from *E. coli*) into the genome was checked by Southern hybridization using a his4 specific probe.

In the case of the non transformed recipient GS115 the probe hybridizes with a fragment of 2.7 kb which contains the point mutated genomic his4 gene (FIG. 3B, lane 1).

In the case of the desired integration of a copy of pAO815-ACC4 into the his4 locus, a 3.6 kb band and 11.8 kb band is expected in Southern blot (FIG. 3A). One of the five clones investigated, designated HWA4, shows the expected hybridization pattern (FIG. 3B, lane 2).

Additionally, the presence of all four acc genes was confirmed by PCR amplification of each of them in the genome of HWA4 (data not shown).

Growth of HWA4 was not inhibited even by 0,1 µg/ml Soraphen A: the transformants containing a copy of the resistance cassette and selected for histidine prototrophy showed undiminished growth on up to 0.1 µg/ml Soraphen.

The presence of the complete i.e the four *E. coli* acc genes accA, accB, accC, and accD containing aox1::acc expression cassette and the resulting simultaneous expression of all these four acc genes from *E. coli* therefore confers to the yeast *Pichia pastoris* a pronounced resistance to the MF-type acetyl-CoA carboxylase inhibitor Soraphen A.

An immediate selection of transformants was feasible: instead of selecting for G418 resistance after transforming *P. pastoris* HWA3 with plasmid pPIC3.5K-BCCP, transformants were directly selected against 0.02 µg/ml Soraphen A. Five Soraphen resistant clones which were analyzed by Southern blot showed exclusively such hybridization patterns which were expected for the integration of plasmid pPIC3.5K-BCCP into one of both his4 loci.

Therefore the described aox1::acc expression cassette is suitable for direct selection for Soraphen A resistance.

Thereby, all prerequisites for the application of this aox1::acc expression cassette and the *E. coli* acc genes accA, accB, accC, and accD being contained therein, respectively, as a selection marker for the transformation of eukaryotes are fulfilled.

Therefore in the following said aox1::acc expression cassette will also be referred to as sorR expression cassette, or sorR cassette, or sorR selection marker, or sorR marker, respectively.

Control

To make sure that the integration of an incomplete set of acc genes into the *Pichia* genome xpression cassettes does not already confer (possibly intermediate) Soraphen resistance, recipient strain GS115 was transformed with plasmid pAO815-ACC3. Transformants selected for histidine prototrophy (among them clone HWA3) were found to be full Soraphen sensitive (i.e. no growth at 0.02 µg/ml). Transformation of *P. pastoris* HWA3 with plasmid pPIC3.5K-BCCP (SEQ ID NO:7) that contains the fourth lacking acc gene under the control of the aox1 promotor, conferred full Soraphen resistance (even against 0.1 µg/ml) to transformants containing one single copy of pPIC3.5K-BCCP integrated into the genome. Transformants containing several integrated copies of this vector displayed intermediate Soraphen resistance. These results did not depend on whether selection was carried out immediately for Soraphen resistance or first for G418 resistance.

EXAMPLE 2

Multi-step Transformations Using an Incomplete sorR Marker

Due to its modular organization with the four single genes accA, accB, accC and accD the sorR selection marker described above is a particularly versatile molecular biological tool. In particular the modular organization allows that the individual elements can be inserted separately into the genome of the cells of the recipient strain which should be transformed. Furthermore, combined to a counter-selectable marker system as the nitrate reductase or orotidylate decarboxylase system (nia, pyr, acs) multi-step transformations may be carried out, e.g. for the successive inactivations of several genes within the same organism.

In principle it is possible to carry out successive transformations with one recipient strain, wherein selection with respect to a particular marker is performed after each individual transformation step. Only cells that have been transformed successfully can grow on the respective selection medium and are available for the subsequent transformations. It is a prerequisite for such a successive transformation that the integration of an incomplete sorR cassette into the recipient's genome does not confer resistance to Soraphen A. This is far from obvious as fungi posses an own ACC activity and it cannot be ruled out a priori that this complements for the activities lacking in the prokaryotic ACC complex.

Figure 4:
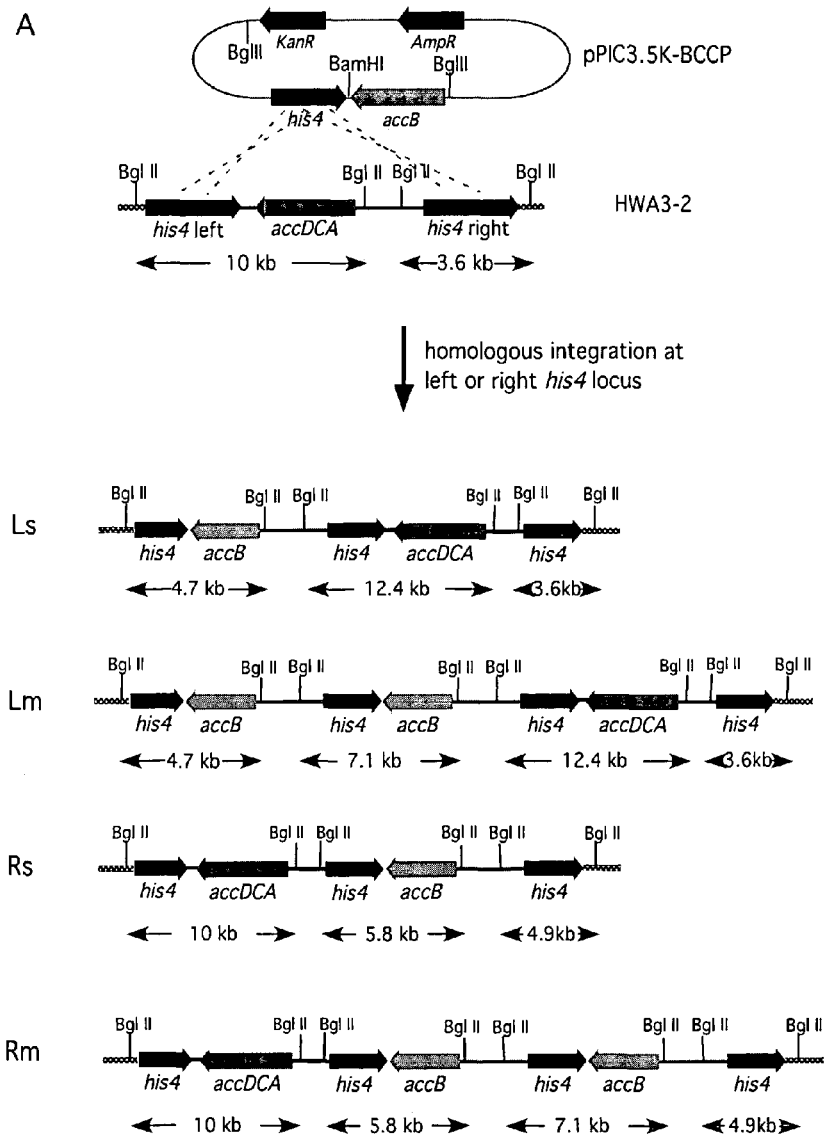

To assess the possibilities of a multi-step transformation employing the sorR markers, cells of *Pichia pastoris* GS115 were transformed with plasmid pAO815-ACC3 that contains all but one of the four prokaryotic acc genes. Transformants were selected for histidine prototrophy. All histidine phototrophic clones analyzed were found to be as sensitive as the recipient strain GS115 against 0.02 µg/ml Soraphen A. One of these clones, termed HWA3 (FIG. 2C), that shows the banding pattern expected for a singular integration into the his4-locus (FIG. 4 and FIG. 5, Lane 3) and in that the presence of all three acc genes was confirmed by PCR, was chosen as the recipient for the second transformation step.

To make sure that the additional introduction of the lacking fourth acc gene (accB) confers resistance to Soraphen A, strain HWA3 was transformed with 6 µg of linear plasmid pPIC3.5K-BCCP containing a G418 resistance cassette. Five of fifteen analyzed G418 resistant clones were sensitive against 0.02 µg/ml Soraphen A; the other ten clones could be divided in such with intermediate and such with fully developed (i.e. analogous to strain HWA4 up to 0.1 µg/ml; exemplary strain HWA3p, FIG. 2D) Soraphen resistance.

Figure 5:
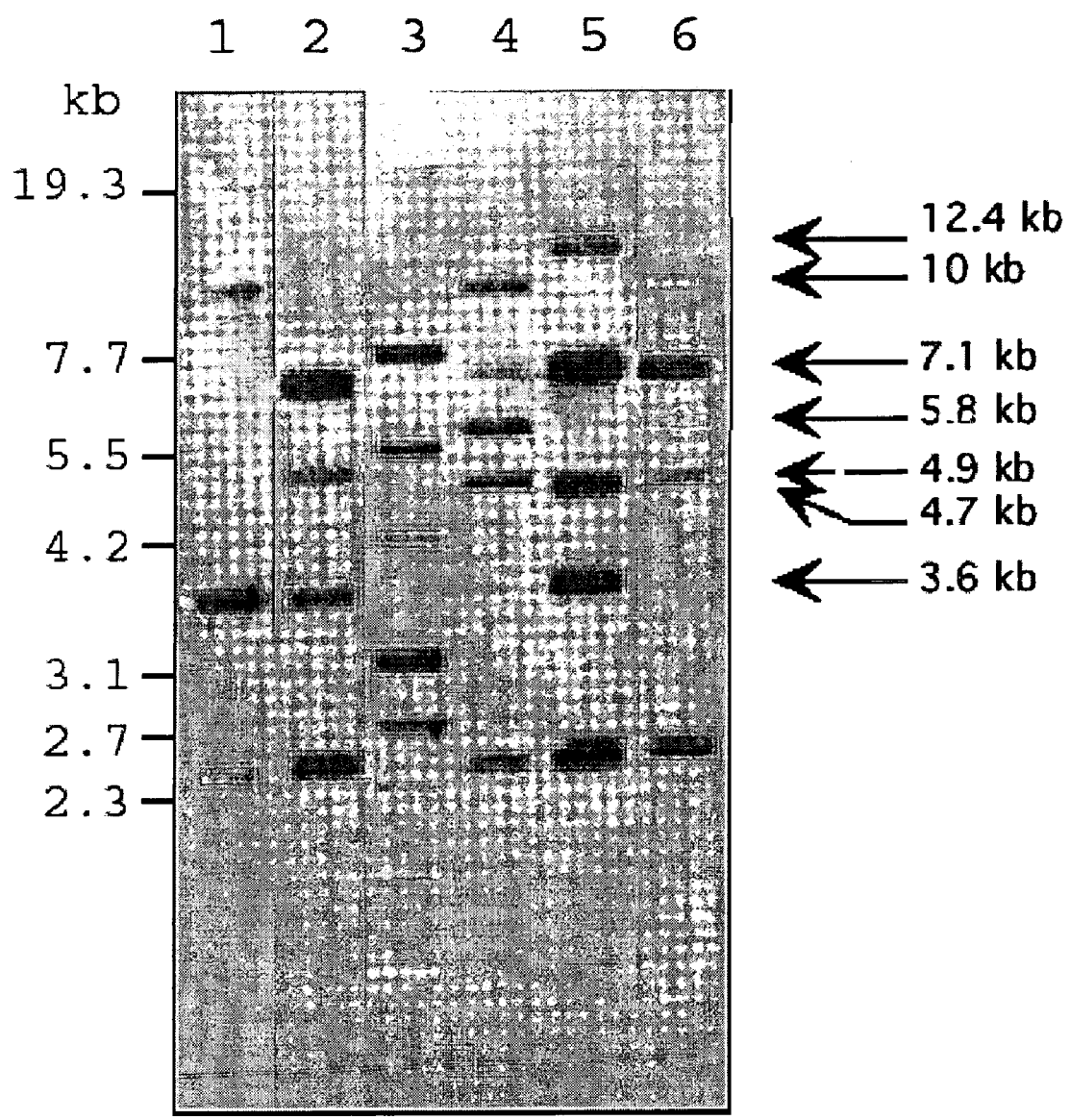

Southern hybridization of BglII-digested chromosomal DNA with a his4-specific probe was used to analyze the integration events giving rise to the observed phenotypes. As the genome of the recipient strain HWA3 contains two his4 loci due to the first transformation step, several homologous recombination events corresponding to different hybridization patterns can be expected: a single copy integration of the plasmid at the "right" (regarding FIG. 4) his4 locus would generate three bands at 10 kb, 5.8 kb and 4.9 kb after digestion with BglII, while a single-copy integration of the plasmid at the left his4 locus generates three bands at 12.4 kb, 4.7 kb and 3.6 kb. Integration of several plasmid copies would generate an additional 7.1 kb band in both cases. While transformants displaying fully developed Soraphen resistance as clon HWA3p (FIG. 5, lane 4) gave rise to hybridization patterns consistent with the integration of a single plasmid copy, banding patterns obtained for clones of intermediate Soraphen resistance were consistent with multiple integrations at either the left (FIG. 5, lane 5) or the right (FIG. 5, lane 6) his4 locus. The hybridization patterns obtained for fully Soraphen sensitive clones indicated either the lack of any plasmid pPIC3.5K-BCCP integration (i.e. false positives of G418 selection; FIG. 5, lane 1) or deletions of sorR marker elements (presumably due to intramolecular DNA rearrangement) (FIG. 5, lane 2).

These described results demonstrate that at least the lack of the BCCP subunit of the prokaryotic MACC complex in *Pichia pastoris* cannot be complemented and that the transformation with only three of the four acc genes does not confer any, not even intermediate resistance to Soraphen.

Therefore, a necessary condition for the application of the sorR markers (Synonyms: sorR expression cassette, sorR cassette) in multi-step transformation experiments is fulfilled.

In an analogous experiment three of the four bacterial acc genes were introduce e.g under selection for chlorate resistance into the nia gene encoding the nitratreductase. Based on that modified recipient strain in a second and a third transformation step, the nia marker as well as the fourth lacking acc gene could be used as selection markers.

EXAMPLE 3

Demonstration that the Correct Stoichiometry of the Four acc Genes is Necessary to Achieve Fully Developed Soraphen A Resistance

*P. pastoris* transformants carrying one integrated copy each of the accA, accC, and accD gene together with several accB genes display only intermediate Soraphen resistance (see example 1, section B "Results", subsection "Control").

Within the course of the multi-step transformation a fundamental and inverse correlation between the level of Soraphen resistance and the number of integrated copies of the fourth acc gene became obvious.

This facts allow in principle a directed selection of transformants with singular integrations.

LITERATURE

1. Al-Feel, W., S. S. Chirala and S. J. Wakil. 1992. Cloning of the yeast FAS3 gene and primary structure of yeast acetyl-CoA carboxylase. Proc Natl Acad Sci USA 89:4534-4538.
2. Gerth, K., N. Bedorf, H. Irschik, G. Hofle and H. Reichenbach. 1994. The Soraphens: a family of novel antifungal compounds from *Sorangium cellulosum* (Myxobacteria). I. Soraphen A1 alpha: fermentation, isolation, biological properties. J Antibiot (Tokyo) 47:23-31.
3. Li, S. J. and J. E. Cronan, Jr. 1992a. The genes encoding the two carboxyltransferase subunits of *Escherichia coli* acetyl-CoA carboxylase. J Biol Chem 267:16841-16847.
4. Li, S. J. and J. E. Cronan, Jr. 1992b. The gene encoding the biotin carboxylase subunit of *Escherichia coli* acetyl-CoA carboxylase. J Biol Chem 267:855-863.
5. Vahlensieck H F, Pridzun L, Reichenbach H & Hinnen A (1994) "Identification of the yeast ACC1 gene product (acetyl-CoA carboxylase) as the target of the polyketide fungicide Soraphen A" Curr Genet 25:95-100.

This disclosure incorporates by reference the entirety of the electronically-submitted 54kb text file entitled "Sequence_Listing" created Apr. 6, 2007.

The invention claimed is:

1. A method for selection for transformed eukaryotic cells, said method comprising:
   (a) subjecting said cells to transformation with one or several genes encoding subunits of a MS-type acetyl-CoA carboxylase (MS-ACC) as selection markers; and
   (b) testing the product of step (a) for resistance to an inhibitor of MF-type acetyl-CoA carboxylases (MF-ACC).

2. The method according to claim 1, wherein each of said genes is localized under the control of one or more eukaryotic expression signals.

3. The method according to claim 1, wherein said genes are localized in an expression vector.

4. The method according to claim 1, wherein said genes are prokaryotic acc genes encoding subunits of the MS-type acetyl-CoA carboxylases of bacteria.

5. The method according to claim 4, wherein the prokaryotic acc genes are selected from the group accA, accB, accC, and accD of *Escherichia coli* acc genes encoding subunits of MS-type acetyl-CoA carboxylase from *E. coli*.

6. The method according to claim 2, wherein said one or more eukaryotic expression signals comprise the methanol-inducible aox1 promoter from yeast cells.

7. The method of claim 3, wherein each single of said genes is located in a separate expression vector.

8. The method according to claim 3, wherein two or more of said genes are combined in the same vector in a tandem configuration, with a resulting vector comprising two or more prokaryotic acc genes.

9. A method for selection for transformed eukaryotic cells, said method comprising:
   (a) subjecting said cells to transformation with one or several genes encoding subunits of a MS-type acetyl-CoA carboxylase (MS-ACC) as selection markers; and
   (b) testing the product of step (a) for resistance to an inhibitor of MF-type acetyl-CoA carboxylases (MF-ACC), wherein the genes are localized in an expression vector and wherein the vector contains all four *Escherichia coli* acc genes accA, accB, accC, and accD in a tandem configuration.

10. The method of claim 1, wherein the inhibitor of MF-type acetyl-CoAcarboxylases (MF-ACC) is the polyketide compound Soraphen.

11. The method of claim 1, wherein the eukaryotic cells are soraphen-sensitive fungi and/or yeast.

12. The method according to claim 11, wherein the soraphen-sensitive eukaryote is yeast *Pichia pastoris*.

* * * * *

SEQUENCE LISTING

<160> NUMBER OF SEQ ID NOS: 15

<210> SEQ ID NO 1
<211> LENGTH: 960

```
<212> TYPE: DNA
<213> ORGANISM: Escherichia coli

<400> SEQUENCE: 1
atgagtctga atttccttga ttttgaacag ccgattgcag agctggaagc gaaaatcgat      60
tctctgactg cggttagccg tcaggatgag aaactggata ttaacatcga tgaagaagtg     120
catcgtctgc gtgaaaaaag cgtagaactg acacgtaaaa tcttcgccga tctcggtgca     180
tggcagattg cgcaactggc acgccatcca cagcgtcctt atacctgga ttacgttcgc      240 ctggcatttg atgaatttga cgaactggct ggcgaccgcg cgtatgcaga cgataaagct     300
atcgtcggtg gtatcgcccg tctcgatggt cgtccggtga tgatcattgg tcatcaaaaa    360
ggtcgtgaaa ccaaagaaaa aattcgccgt aactttggta tgccagcgcc agaaggttac    420
cgcaaagcac tgcgtctgat gcaaatggct gaacgcttta gatgcctat catcacctttt    480 atcgacaccc cggggcttta tcctggcgtg ggcgcagaag agcgtggtca gtctgaagcc    540
attgcacgca acctgcgtga atgtctcgc ctcggcgtac cggtagtttg tacggttatc     600
ggtgaaggtg ttctggcgg tgcgctggcg attggcgtgg gcgataaagt gaatatgctg     660
caatacagca cctattccgt tatctcgccg gaaggttgtg cgtccattct gtggaagagc    720
gccgacaaag cgccgctggc ggctgaagcg atgggtatca ttgctccgcg tctgaaagaa    780
ctgaaactga tcgactccat catcccggaa ccactgggtg gtgctcaccg taacccggaa    840
gcgatggcgg catcgttgaa agcgcaactg ctggcggatc tggccgatct cgacgtgtta    900
agcactgaag atttaaaaaa tcgtcgttat cagcgcctga tgagctacgg ttacgcgtaa    960

<210> SEQ ID NO 2
<211> LENGTH: 471
<212> TYPE: DNA
<213> ORGANISM: Escherichia coli

<400> SEQUENCE: 2
atggatattc gtaagattaa aaaactgatc gagctggttg aagaatcagg catctccgaa      60
ctggaaattt ctgaaggcga agagtcagta cgcattagcc gtgcagctcc tgccgcaagt     120
ttccctgtga tgcaacaagc ttacgctgca ccaatgatgc agcagccagc tcaatctaac    180
gcagccgctc cggcgaccgt tccttccatg gaagcgccag cagcagcgga atcagtggt     240 cacatcgtac gttccccgat ggttggtact ttctaccgca cccaagcccc ggacgcaaaa    300
gcgttcatcg aagtgggtca gaaagtcaac gtgggcgata ccctgtgcat cgttgaagcc    360
atgaaaatga tgaaccagat cgaagcggac aaatccggta ccgtgaaagc aattctggtc    420
gaaagtggac aaccggtaga atttgacgag ccgctggtcg tcatcgagta a              471

<210> SEQ ID NO 3
<211> LENGTH: 1350
<212> TYPE: DNA
<213> ORGANISM: Escherichia coli

<400> SEQUENCE: 3
atgctggata aaattgttat tgccaaccgc ggcgagattg cattgcgtat tcttcgtgcc      60
tgtaaagaac tgggcatcaa gactgtcgct gtgcactcca gcgcggatcg cgatctaaaa     120
cacgtattac tggcagatga acggtctgt attggccctg ctccgtcagt aaaaagttat    180
ctgaacatcc cggcaatcat cagcgccgct gaaatcaccg gcgcagtagc aatccatccg    240
ggttacggct cctctcccga gaacgccaac tttgccgagc aggttgaacg ctccggcttt    300
atcttcattg gcccgaaagc agaaaccatt cgcctgatgg gcgacaaagt atccgcaatc    360
```

```
gcggcgatga aaaaagcggg cgtcccttgc gtaccgggtt ctgacggccc gctgggcgac      420
gatatggata aaaccgtgc cattgctaaa cgcattggtt atccggtgat tatcaaagcc       480
tccggcggcg cggcggtcg cggtatcgcg cgtagtgcgcg cgacgctga actggcacaa      540 tccatctcca tgacccgtgc ggaagcgaaa gctgctttca gcaacgatat ggtttacatg     600
gagaaatacc tggaaaatcc tcgccacgtc gagattcagg tactggctga cggtcagggc    660
aacgctatct atctggcgga acgtgactgc tccatgcaac gccgccacca gaaagtggtc    720
gaagaagcgc cagcaccggg cattaccccg gaactgcgtc gctacatcgg cgaacgttgc    780
gctaaagcgt gtgttgatat cggctatcgc ggtgcaggta ctttcgagtt cctgttcgaa    840
aacggcgagt ctatttcat cgaaatgaac acccgtattc aggtagaaca cccggttaca     900
gaaatgatca ccggcgttga cctgatcaaa gaacagctgc gtatcgctgc cggtcaaccg    960
ctgtcgatca agcaagaaga agttcacgtt cgcggccatg cggtggaatg tcgtatcaac   1020
gccgaagatc cgaacaccttt cctgccaagt ccgggcaaaa tcacccgttt ccacgcacct  1080
ggcggttttg cgtacgttg ggagtctcat atctacgcgg gctacaccgt accgccgtac    1140
tatgactcaa tgatcggtaa gctgatttgc tacggtgaaa accgtgacgt ggcgattgcc   1200
cgcatgaaga atgcgctgca ggagctgatc atcgacggta tcaaaaccaa cgttgatctg   1260
cagatccgca tcatgaatga cgagaacttc cagcatggtg gcactaacat ccactatctg   1320
gagaaaaaac tcggtcttca ggaaaaataa                                    1350

<210> SEQ ID NO 4
<211> LENGTH: 918
<212> TYPE: DNA
<213> ORGANISM: Escherichia coli

<400> SEQUENCE: 4
atgagctgga ttgaacgaat taaaagcaac attactccca cccgcaaggc gagcattcct     60
gaaggggtgt ggactaagtg tgatagctgc ggtcaggttt tataccgcgc tgagctggaa    120
cgtaatcttg aggtctgtcc gaagtgtgac catcacatgc gtatgacagc gcgtaatcgc    180
ctgcatagcc tgttagatga aggaagcctt gtggagctgg gtagcagcgt tgagccgaaa    240
gatgtgctga gtttcgtga ctccaagaag tataaagacc gtctggcatc tgcgcagaaa    300
gaaaccggcg aaaaagatgc gctggtggtg atgaaaggca ctctgtatgg aatgccggtt    360
gtcgctgcgg cattcgagtt cgcctttatg ggcggttcaa tggggtctgt tgtgggtgca    420
cgtttcgtgc gtgccgttga gcaggcgctg aagataact gcccgctgat ctgcttctcc    480
gcctctggtg gcgcacgtat gcaggaagca ctgatgtcgc tgatgcagat ggcgaaaacc    540
tctgcggcac tggcaaaaat gcaggagcgc ggcttgccgt acatctccgt gctgaccgac    600
ccgacgatgg gcggtgtttc tgcaagtttc gccatgctgg gcgatctcaa catcgctgaa    660
ccgaaagcgt taatcgcttt gccggtccgc gtgttatcga acagaaccgt tcgcgaaaaa   720
ctgccgcctg gattccagcg cagtgaattc ctgatcgaga aaggcgcgat cgacatgatc    780
gtccgtcgtc cggaaatgcg cctgaaactg gcgagcattc tggcgaagtt gatgaatctg    840
ccagcgccga atcctgaagc gccgcgtgaa ggcgtagtgg tacccccggt accggatcag    900
gaacctgagg cctgataa                                                 918

<210> SEQ ID NO 5
<211> LENGTH: 13518
<212> TYPE: DNA
<213> ORGANISM: Artificial
```

<220> FEATURE:
<223> OTHER INFORMATION: Chemically Synthesized

<400> SEQUENCE: 5

| | | | | | |
|---|---|---|---|---|---|
| agatctaaca | tccaaagacg | aaaggttgaa | tgaaacctttt | ttgccatccg | acatccacag | 60 |
| gtccattctc | acacataagt | gccaaacgca | acaggagggg | atacactagc | agcagaccgt | 120 |
| tgcaaacgca | ggacctccac | tcctcttctc | ctcaacaccc | acttttgcca | tcgaaaaacc | 180 |
| agcccagtta | ttgggcttga | ttggagctcg | ctcattccaa | ttccttctat | taggctacta | 240 |
| acaccatgac | tttattagcc | tgtctatcct | ggcccccctg | gcgaggttca | tgtttgttta | 300 |
| tttccgaatg | caacaagctc | cgcattacac | ccgaacatca | ctccagatga | gggctttctg | 360 |
| agtgtggggt | caaatagttt | catgttcccc | aaatggccca | aaactgacag | tttaaacgct | 420 |
| gtcttggaac | ctaatatgac | aaaagcgtga | tctcatccaa | gatgaactaa | gtttggttcg | 480 |
| ttgaaatgct | aacggccagt | tggtcaaaaa | gaaacttcca | aaagtcggca | taccgtttgt | 540 |
| cttgtttggt | attgattgac | gaatgctcaa | aaataatctc | attaatgctt | agcgcagtct | 600 |
| ctctatcgct | tctgaacccc | ggtgcacctg | tgccgaaacg | caaatgggga | acacccgct | 660 |
| ttttggatga | ttatgcattg | tctccacatt | gtatgcttcc | aagattctgg | tgggaatact | 720 |
| gctgatagcc | taacgttcat | gatcaaaatt | taactgttct | aaccccctact | tgacagcaat | 780 |
| atataaacag | aaggaagctg | ccctgtctta | aaccttttt | tttatcatca | ttattagctt | 840 |
| actttcataa | ttgcgactgg | ttccaattga | caagcttttg | attttaacga | cttttaacga | 900 |
| caacttgaga | agatcaaaaa | acaactaatt | attcgaaacg | aggaattcac | catgagtctg | 960 |
| aatttccttg | attttgaaca | gccgattgca | gagctggaag | cgaaaatcga | ttctctgact | 1020 |
| gcggttagcc | gtcaggatga | gaaactggat | attaacatcg | atgaagaagt | gcatcgtctg | 1080 |
| cgtgaaaaaa | gcgtagaact | gacacgtaaa | atcttcgccg | atctcggtgc | atggcagatt | 1140 |
| gcgcaactgg | cacgccatcc | acagcgtcct | tataccctgg | attacgttcg | cctggcatt | 1200 |
| gatgaatttg | acgaactggc | tggcgaccgc | gcgtatgcag | acgataaagc | tatcgtcggt | 1260 |
| ggtatcgccc | gtctcgatgg | tcgtccggtg | atgatcattg | gtcatcaaaa | aggtcgtgaa | 1320 |
| accaaagaaa | aaattcgccg | taactttggt | atgccagcgc | cagaaggtta | ccgcaaagca | 1380 |
| ctgcgtctga | tgcaaatggc | tgaacgcttt | aagatgccta | tcatcacctt | tatcgacacc | 1440 |
| ccgggggctt | atcctggcgt | gggcgcagaa | gagcgtggtc | agtctgaagc | cattgcacgc | 1500 |
| aacctgcgtg | aaatgtctcg | cctcggcgta | ccggtagttt | gtacggttat | cggtgaaggt | 1560 |
| ggttctggcg | gtgcgctggc | gattggcgtg | ggcgataaag | tgaatatgct | gcaatacagc | 1620 |
| acctattccg | ttatctcgcc | ggaaggttgt | gcgtccattc | tgtggaagag | cgccgacaaa | 1680 |
| gcgccgctgg | cggctgaagc | gatgggtatc | attgctccgc | gtctgaaaga | actgaaactg | 1740 |
| atcgactcca | tcatcccgga | accactgggt | ggtgctcacc | gtaacccgga | agcgatggcg | 1800 |
| gcatcgttga | aagcgcaact | gctggcggat | ctggccgatc | tcgacgtgtt | aagcactgaa | 1860 |
| gatttaaaaa | atcgtcgtta | tcagcgcctg | atgagctacg | gttacgcgta | agaattcgcc | 1920 |
| ttagacatga | ctgttcctca | gttcaagttg | ggcacttacg | agaagaccgg | tcttgctaga | 1980 |
| ttctaatcaa | gaggatgtca | gaatgccatt | tgcctgagag | atgcaggctt | cattttttgat | 2040 |
| acttttttat | ttgtaaccta | tatagtatag | gatttttttt | gtcatttgt | ttcttctcgt | 2100 |
| acgagcttgc | tcctgatcag | cctatctcgc | agctgatgaa | tatcttgtgg | taggggtttg | 2160 |
| ggaaaatcat | tcgagtttga | tgtttttctt | ggtatttccc | actcctcttc | agagtacaga | 2220 |
| agattaagtg | agacgttcgt | ttgtgcggat | ctaacatcca | aagacgaaag | gttgaatgaa | 2280 |

```
accttttgc catccgacat ccacaggtcc attctcacac ataagtgcca aacgcaacag    2340
gaggggatac actagcagca gaccgttgca aacgcaggac ctccactcct cttctcctca    2400
acacccactt tgccatcga aaaccagcc cagttattgg gcttgattgg agctcgctca     2460
ttccaattcc ttctattagg ctactaacac catgacttta ttagcctgtc tatcctggcc    2520
cccctggcga ggttcatgtt tgtttatttc cgaatgcaac aagctccgca ttacacccga    2580
acatcactcc agatgagggc tttctgagtg tggggtcaaa tagtttcatg ttccccaaat    2640
ggcccaaaac tgacagttta aacgctgtct tggaacctaa tatgacaaaa gcgtgatctc    2700
atccaagatg aactaagttt ggttcgttga aatgctaacg gccagttggt caaaagaaa    2760 cttccaaaag tcggcatacc gtttgtcttg tttggtattg attgacgaat gctcaaaaat    2820
aatctcatta atgcttagcg cagtctctct atcgcttctg aaccccggtg cacctgtgcc    2880
gaaacgcaaa tggggaaaca cccgcttttt ggatgattat gcattgtctc cacattgtat    2940
gcttccaaga ttctggtggg aatactgctg atagcctaac gttcatgatc aaaatttaac    3000
tgttctaacc cctacttgac agcaatatat aaacagaagg aagctgccct gtcttaaacc    3060
ttttttttta tcatcattat tagcttactt tcataattgc gactggttcc aattgacaag    3120
cttttgattt taacgacttt taacgacaac ttgagaagat caaaaaacaa ctaattattc    3180
gaaacgagga attcaccatg ctggataaaa ttgttattgc caaccgcggc gagattgcat    3240
tgcgtattct tcgtgcctgt aaagaactgg gcatcaagac tgtcgctgtg cactccagcg    3300
cggatcgcga tctaaaacac gtattactgg cagatgaaac ggtctgtatt ggccctgctc    3360
cgtcagtaaa aagttatctg aacatcccgg caatcatcag cgccgctgaa atcaccggcg    3420
cagtagcaat ccatccgggt tacgcttcc tctccgagaa cgccaacttt gccgagcagg     3480
ttgaacgctc cggctttatc ttcattggcc cgaaagcaga aaccattcgc ctgatgggcg    3540
acaaagtatc cgcaatcgcg gcgatgaaaa aagcgggcgt cccttgcgta ccgggttctg    3600
acggcccgct gggcgacgat atggataaaa accgtgccat tgctaaacgc attggttatc    3660
cggtgattat caaagcctcc ggcggcgcg cggtcgcgg tatgcgcgta gtgcgcggcg     3720
acgctgaact ggcacaatcc atctccatga cccgtgcgga agcgaaagct gctttcagca    3780
acgatatggt ttacatggag aaatacctgg aaaatcctcg ccacgtcgag attcaggtac    3840
tggctgacgg tcagggcaac gctatctatc tggcggaacg tgactgctcc atgcaacgcc    3900
gccaccagaa agtggtcgaa gaagcgccag caccgggcat taccccggaa ctgcgtcgct    3960
acatcggcga acgttgcgct aaagcgtgtg ttgatatcgg ctatcgcggt gcaggtactt    4020
tcgagttcct gttcgaaaac ggcgagttct atttcatcga aatgaacacc cgtattcagg    4080
tagaacaccc ggttacagaa atgatcaccg gcgttgacct gatcaaagaa cagctgcgta    4140
tcgctgccgg tcaaccgctg tcgatcaagc aagaagaagt tcacgttcgc ggccatgcgg    4200
tggaatgtcg tatcaacgcc gaagatccga acaccttcct gccaagtccg ggcaaaatca    4260
cccgttccca cgcacctggc ggttttggcg tacgttggga gtctcatatc tacgcgggct    4320
acaccgtacc gccgtactat gactcaatga tcggtaagct gatttgctac ggtgaaaacc    4380
gtgacgtggc gattgcccgc atgaagaatg cgctgcagga gctgatcatc gacggtatca    4440
aaaccaacgt tgatctgcag atccgcatca tgaatgacga gaacttccag catggtggca    4500
ctaacatcca ctatctggag aaaaaactcg gtcttcagga aaaataagaa ttcgccttag    4560
acatgactgt tcctcagttc aagttgggca cttacgagaa gaccggtctt gctagattct    4620
aatcaagagg atgtcagaat gccatttgcc tgagagatgc aggcttcatt tttgatactt    4680
```

```
ttttatttgt aacctatata gtataggatt ttttttgtca ttttgtttct tctcgtacga    4740
gcttgctcct gatcagccta tctcgcagct gatgaatatc ttgtggtagg ggtttgggaa    4800
aatcattcga gtttgatgtt tttcttggta tttcccactc ctcttcagag tacagaagat    4860
taagtgagac gttcgtttgt gcggatctaa catccaaaga cgaaaggttg aatgaaacct    4920
ttttgccatc cgacatccac aggtccattc tcacacataa gtgccaaacg caacaggagg    4980
ggatacacta gcagcagacc gttgcaaacg caggacctcc actcctcttc tcctcaacac    5040
ccacttttgc catcgaaaaa ccagcccagt tattgggctt gattggagct cgctcattcc    5100
aattccttct attaggctac taacaccatg actttattag cctgtctatc ctggcccccc    5160
tggcgaggtt catgtttgtt tatttccgaa tgcaacaagc tccgcattac acccgaacat    5220
cactccagat gagggctttc tgagtgtggg gtcaaatagt ttcatgttcc ccaaatggcc    5280
caaaactgac agtttaaacg ctgtcttgga acctaatatg acaaaagcgt gatctcatcc    5340
aagatgaact aagtttggtt cgttgaaatg ctaacggcca gttggtcaaa agaaacttc    5400 caaaagtcgg cataccgttt gtcttgtttg gtattgattg acgaatgctc aaaaataatc    5460
tcattaatgc ttagcgcagt ctctctatcg cttctgaacc ccggtgcacc tgtgccgaaa    5520
cgcaaatggg gaaacacccg ctttttggat gattatgcat tgtctccaca ttgtatgctt    5580
ccaagattct ggtgggaata ctgctgatag cctaacgttc atgatcaaaa tttaactgtt    5640
ctaaccccta cttgacagca atatataaac agaaggaagc tgccctgtct taaaccttt    5700 ttttatcat cattattagc ttactttcat aattgcgact ggttccaatt gacaagcttt    5760
tgattttaac gacttttaac gacaacttga aagatcaaa aaacaactaa ttattcgaaa    5820
cgaggaattg accatgagct ggattgaacg aattaaaagc aacattactc ccacccgcaa    5880
ggcgagcatt cctgaagggg tgtggactaa gtgtgatagc tgcggtcagg ttttataccg    5940
cgctgagctg aacgtaatc ttgaggtctg tccgaagtgt gaccatcaca tgcgtatgac    6000
agcgcgtaat cgcctgcata gcctgttaga tgaaggaagc cttgtggagc tgggtagcag    6060
cgttgagccg aaagatgtgc tgaagtttcg tgactccaag aagtataaag accgtctggc    6120
atctgcgcag aaagaaaccg gcgaaaaaga tgcgctggtg gtgatgaaag gcactctgta    6180
tggaatgccg gttgtcgctg cggcattcga gttcgccttt atgggcggtt caatggggtc    6240
tgttgtgggt gcacgtttcg tgcgtgccgt tgagcaggcg ctggaagata actgcccgct    6300
gatctgcttc tccgcctctg gtggcgcacg tatgcaggaa gcactgatgt cgctgatgca    6360
gatggcgaaa acctctgcgg cactggcaaa aatgcaggag cgcggcttgc cgtacatctc    6420
cgtgctgacc gacccgacga tgggcggtgt ttctgcaagt ttcgccatgc tgggcgatct    6480
caacatcgct gaaccgaaag cgttaatcgc tttgccggtc cgcgtgttat cgaacagaac    6540
cgttcgcgaa aaactgccgc ctggattcca gcgcagtgaa ttcctgatcg agaaaggcgc    6600
gatcgacatg atcgtccgtc gtccggaaat gcgcctgaaa ctggcgagca ttctggcgaa    6660
gttgatgaat ctgccagcgc cgaatcctga agcgccgcgt gaaggcgtag tggtaccccc    6720
ggtaccggat caggaacctg aggcctgata caattcgcc ttagacatga ctgttcctca    6780
gttcaagttg ggcacttacg agaagaccgg tcttgctaga ttctaatcaa gaggatgtca    6840
gaatgccatt tgcctgagag atgcaggctt catttttgat acttttttat ttgtaaccta    6900
tatagtatag gattttttttt gtcattttgt ttcttctcgt acgagcttgc tcctgatcag    6960
cctatctcgc agctgatgaa tatcttgtgg taggggtttg ggaaaatcat tcgagtttga    7020
tgtttttctt ggtatttccc actcctcttc agagtacaga agattaagtg agacgttcgt    7080
```

```
ttgtgcggat cctaatgcgg tagtttatca cagttaaatt gctaacgcag tcaggcaccg   7140
tgtatgaaat ctaacaatgc gctcatcgtc atcctcggca ccgtcaccct ggatgctgta   7200
ggcataggct tggttatgcc ggtactgccg ggcctcttgc gggatatcgt ccattccgac   7260
agcatcgcca gtcactatgg cgtgctgcta gcgctatatg cgttgatgca atttctatgc   7320
gcacccgttc tcggagcact gtccgaccgc tttggccgcc gcccagtcct gctcgcttcg   7380
ctacttggag ccactatcga ctacgcgatc atggcgacca cacccgtcct gtggatctat   7440
cgaatctaaa tgtaagttaa aatctctaaa taattaaata gtcccagtt tctccatacg    7500
aaccttaaca gcattgcggt gagcatctag accttcaaca gcagccagat ccatcactgc   7560
ttggccaata tgtttcagtc cctcaggagt tacgtcttgt gaagtgatga acttctggaa   7620
ggttgcagtg ttaactccgc tgtattgacg ggcatatccg tacgttggca aagtgtggtt   7680
ggtaccggag gagtaatctc cacaactctc tggagagtag gcaccaacaa acacagatcc   7740
agcgtgttgt acttgatcaa cataagaaga agcattctcg atttgcagga tcaagtgttc   7800
aggagcgtac tgattggaca tttccaaagc ctgctcgtag gttgcaaccg atagggttgt   7860
agagtgtgca atacacttgc gtacaatttc aacccttggc aactgcacag cttggttgtg   7920
aacagcatct tcaattctgg caagctcctt gtctgtcata tcgacagcca acagaatcac   7980
ctgggaatca ataccatgtt cagcttgaga cagaaggtct gaggcaacga aatctggatc   8040
agcgtattta tcagcaataa ctagaacttc agaaggccca gcaggcatgt caatactaca   8100
cagggctgat gtgtcatttt gaaccatcat cttggcagca gtaacgaact ggtttcctgg   8160
accaaatatt ttgtcacact taggaacagt ttctgttccg taagccatag cagctactgc   8220
ctgggcgcct cctgctagca cgatacactt agcaccaacc ttgtgggcaa cgtagatgac   8280
ttctggggta agggtaccat ccttcttagg tggagatgca aaaacaattt ctttgcaacc   8340
agcaactttg gcaggaacac ccagcatcag ggaagtggaa ggcagaattg cggttccacc   8400
aggaatatag aggccaactt tctcaatagg tcttgcaaaa cgagagcaga ctacaccagg   8460
gcaagtctca acttgcaacg tctccgttag ttgagcttca tggaatttcc tgacgttatc   8520
tatagagaga tcaatggctc tcttaacgtt atctggcaat tgcataagtt cctctgggaa   8580
aggagcttct aacacaggtg tcttcaaagc gactccatca aacttggcag ttagttctaa   8640
aagggctttg tcaccatttt gacgaacatt gtcgacaatt ggtttgacta attccataat   8700
ctgttccgtt ttctggatag gacgacgaag ggcatcttca attcttgtg aggaggcctt    8760
agaaacgtca attttgcaca attcaatacg accttcagaa gggacttctt taggtttgga   8820
ttcttcttta ggttgttcct tggtgtatcc tggcttggca tctccttttcc ttctagtgac  8880
ctttagggac ttcatatcca ggtttctctc cacctcgtcc aacgtcacac cgtacttggc   8940
acatctaact aatgcaaaat aaaataagtc agcacattcc caggctatat cttccttgga   9000
tttagcttct gcaagttcat cagcttcctc cctaatttta gcgttcaaca aaacttcgtc   9060
gtcaaataac cgtttggtat aagaaccttc tggagcattg ctcttacgat cccacaaggt   9120
ggcttccatg gctctaagac ccttgattg gccaaaacag gaagtgcgtt ccaagtgaca    9180
gaaaccaaca cctgtttgtt caaccacaaa tttcaagcag tctccatcac aatccaattc   9240
gatacccagc aactttgag ttgctccaga tgtagcacct ttataccaca aaccgtgacg    9300
acgagattgg tagactccag tttgtgtcct tatagcctcc ggaatagact ttttggacga   9360
gtacaccagg cccaacgagt aattagaaga gtcagccacc aaagtagtga atagaccatc   9420
ggggcggtca gtagtcaaag acgccaacaa aatttcactg acagggaact ttttgacatc   9480
```

```
ttcagaaagt tcgtattcag tagtcaattg ccgagcatca ataatgggga ttataccaga    9540
agcaacagtg gaagtcacat ctaccaactt tgcggtctca gaaaaagcat aaacagttct    9600
actaccgcca ttagtgaaac ttttcaaatc gcccagtgga gaagaaaaag gcacagcgat    9660
actagcatta gcgggcaagg atgcaacttt atcaaccagg gtcctataga taaccctagc    9720
gcctgggatc atcctttgga caactctttc tgccaaatct aggtccaaaa tcacttcatt    9780
gataccatta ttgtacaact tgagcaagtt gtcgatcagc tcctcaaatt ggtcctctgt    9840
aacggatgac tcaacttgca cattaacttg aagctcagtc gattgagtga acttgatcag    9900
gttgtgcagc tggtcagcag catagggaaa cacggctttt cctaccaaac tcaaggaatt    9960
atcaaactct gcaacacttg cgtatgcagg tagcaaggga aatgtcatac ttgaagtcgg   10020
acagtgagtg tagtcttgag aaattctgaa gccgtatttt tattatcagt gagtcagtca   10080
tcaggagatc ctctacgccg gacgcatcgt ggccggcatc accggcgcca caggtgcggt   10140
tgctggcgcc tatatcgccg acatcaccga tggggaagat cgggctcgcc acttcgggct   10200
catgagcgct tgtttcggcg tgggtatggt ggcaggcccc gtggccgggg gactgttggg   10260
cgccatctcc ttgcatgcac cattccttgc ggcggcggtg ctcaacgccc tcaacctact   10320
actgggctgc ttcctaatgc aggagtcgca taagggagag cgtcgagtat ctatgattgg   10380
aagtatggga atggtgatac ccgcattctt cagtgtcttg aggtctccta tcagattatg   10440
cccaactaaa gcaaccggag gaggagattt catggtaaat ttctctgact tttggtcatc   10500
agtagactcg aactgtgaga ctatctcggt tatgacagca gaaatgtcct tcttggagac   10560
agtaaatgaa gtcccaccaa taagaaatc cttgttatca ggaacaaact tcttgtttcg   10620
aacttttcg gtgccttgaa ctataaaatg tagagtggat atgtcgggta ggaatggagc   10680
gggcaaatgc ttaccttctg gaccttcaag aggtatgtag ggtttgtaga tactgatgcc   10740
aacttcagtg acaacgttgc tatttcgttc aaaccattcc gaatccagag aaatcaaagt   10800
tgtttgtcta ctattgatcc aagccagtgc ggtcttgaaa ctgacaatag tgtgctcgtg   10860
ttttgaggtc atctttgtat gaataaatct agtctttgat ctaaataatc ttgacgagcc   10920
aaggcgataa ataccaaat ctaaaactct tttaaaacgt taaaaggaca agtatgtctg   10980
cctgtattaa accccaaatc agctcgtagt ctgatcctca tcaacttgag gggcactatc   11040
ttgtttttaga gaaatttgcg gagatgcgat atcgagaaaa aggtacgctg atttttaaacg   11100
tgaaatttat ctcaagatct gctgcctcgc gcgtttcggt gatgacggtg aaaacctctg   11160
acacatgcag ctcccggaga cggtcacagc ttgtctgtaa gcggatgccg ggagcagaca   11220
agcccgtcag ggcgcgtcag cgggtgttgg cgggtgtcgg ggcgcagcca tgacccagtc   11280
acgtagcgat agcggagtgt atactggctt aactatgcgg catcagagca gattgtactg   11340
agagtgcacc atatgcggtg tgaaataccg cacagatgcg taaggagaaa ataccgcatc   11400
aggcgctctt ccgcttcctc gctcactgac tcgctgcgct cggtcgttcg gctgcggcga   11460
gcggtatcag ctcactcaaa ggcggtaata cggttatcca cagaatcagg ggataacgca   11520
ggaaagaaca tgtgagcaaa aggccagcaa aaggccagga accgtaaaaa ggccgcgttg   11580
ctggcgtttt tccataggct ccgcccccct gacgagcatc acaaaaatcg acgctcaagt   11640
cagaggtggc gaaacccgac aggactataa agataccagg cgtttccccc tggaagctcc   11700
ctcgtgcgct ctcctgttcc gaccctgccg cttaccggat acctgtccgc ctttctccct   11760
tcgggaagcg tggcgctttc tcaatgctca cgctgtaggt atctcagttc ggtgtaggtc   11820
gttcgctcca agctgggctg tgtgcacgaa ccccccgttc agcccgaccg ctgcgcctta   11880
```

| | |
|---|---|
| tccggtaact atcgtcttga gtccaacccg gtaagacacg acttatcgcc actggcagca | 11940 |
| gccactggta acaggattag cagagcgagg tatgtaggcg gtgctacaga gttcttgaag | 12000 |
| tggtggccta actacggcta cactagaagg acagtatttg gtatctgcgc tctgctgaag | 12060 |
| ccagttacct tcggaaaaag agttggtagc tcttgatccg gcaaacaaac caccgctggt | 12120 |
| agcggtggtt ttttgtttg caagcagcag attacgcgca gaaaaaaagg atctcaagaa | 12180 |
| gatcctttga tcttttctac ggggtctgac gctcagtgga acgaaaactc acgttaaggg | 12240 |
| attttggtca tgagattatc aaaaaggatc ttcacctaga tccttttaaa ttaaaaatga | 12300 |
| agttttaaat caatctaaag tatatatgag taaacttggt ctgacagtta ccaatgctta | 12360 |
| atcagtgagg cacctatctc agcgatctgt ctatttcgtt catccatagt tgcctgactc | 12420 |
| cccgtcgtgt agataactac gatacgggag ggcttaccat ctggccccag tgctgcaatg | 12480 |
| ataccgcgag acccacgctc accggctcca gatttatcag caataaacca gccagccgga | 12540 |
| agggccgagc gcagaagtgg tcctgcaact ttatccgcct ccatccagtc tattaattgt | 12600 |
| tgccgggaag ctagagtaag tagttcgcca gttaatagtt tgcgcaacgt tgttgccatt | 12660 |
| gctgcaggca tcgtggtgtc acgctcgtcg tttggtatgg cttcattcag ctccggttcc | 12720 |
| caacgatcaa ggcgagttac atgatccccc atgttgtgca aaaagcggt tagctccttc | 12780 |
| ggtcctccga tcgttgtcag aagtaagttg gccgcagtgt tatcactcat ggttatggca | 12840 |
| gcactgcata attctcttac tgtcatgcca tccgtaagat gcttttctgt gactggtgag | 12900 |
| tactcaacca agtcattctg agaatagtgt atgcggcgac cgagttgctc ttgcccggcg | 12960 |
| tcaacacggg ataataccgc gccacatagc agaactttaa aagtgctcat cattggaaaa | 13020 |
| cgttcttcgg ggcgaaaact ctcaaggatc ttaccgctgt tgagatccag ttcgatgtaa | 13080 |
| cccactcgtg cacccaactg atcttcagca tcttttactt tcaccagcgt ttctgggtga | 13140 |
| gcaaaaacag gaaggcaaaa tgccgcaaaa aagggaataa gggcgacacg gaaatgttga | 13200 |
| atactcatac tcttcctttt tcaatattat tgaagcattt atcagggtta ttgtctcatg | 13260 |
| agcggataca tatttgaatg tatttagaaa aataaacaaa tagggggttcc gcgcacattt | 13320 |
| ccccgaaaag tgccacctga cgtctaagaa accattatta tcatgacatt aacctataaa | 13380 |
| aataggcgta tcacgaggcc ctttcgtctt caagaattaa ttctcatgtt tgacagctta | 13440 |
| tcatcgataa gctgactcat gttggtattg tgaaatagac gcagatcggg aacactgaaa | 13500 |
| aataacagtt attattcg | 13518 |

<210> SEQ ID NO 6
<211> LENGTH: 15275
<212> TYPE: DNA
<213> ORGANISM: Artificial
<220> FEATURE:
<223> OTHER INFORMATION: Chemically Synthesized

<400> SEQUENCE: 6

| | |
|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |

```
gtcttggaac ctaatatgac aaaagcgtga tctcatccaa gatgaactaa gtttggttcg      480
ttgaaatgct aacgccagt  tggtcaaaaa gaaacttcca aaagtcggca taccgtttgt      540
cttgtttggt attgattgac gaatgctcaa aaataatctc attaatgctt agcgcagtct      600
ctctatcgct tctgaacccc ggtgcacctg tgccgaaacg caaatgggga acacccgct       660 ttttggatga ttatgcattg tctccacatt gtatgcttcc aagattctgg tgggaatact      720
gctgatagcc taacgttcat gatcaaaatt taactgttct aacccctact tgacagcaat      780
atataaacag aaggaagctg ccctgtctta aacctttttt tttatcatca ttattagctt      840
actttcataa ttgcgactgg ttccaattga caagcttttg attttaacga cttttaacga      900
caacttgaga agatcaaaaa acaactaatt attcgaaacg aggaattcac catgagtctg      960
aatttccttg attttgaaca gccgattgca gagctggaag cgaaaatcga ttctctgact     1020
gcggttagcc gtcaggatga gaaactggat attaacatcg atgaagaagt gcatcgtctg     1080
cgtgaaaaaa gcgtagaact gacacgtaaa atcttcgccg atctcggtgc atggcagatt     1140
gcgcaactgg cacgccatcc acagcgtcct tatacccctgg attacgttcg cctggcattt     1200
gatgaatttg acgaactggc tggcgaccgc gcgtatgcag acgataaagc tatcgtcggt     1260
ggtatcgccc gtctcgatgg tcgtccggtg atgatcattg gtcatcaaaa aggtcgtgaa     1320
accaaagaaa aaattcgccg taactttggt atgccagcgc cagaaggtta ccgcaaagca     1380
ctgcgtctga tgcaaatggc tgaacgcttt aagatgccta tcatcacctt tatcgacacc     1440
ccgggggctt atcctggcgt gggcgcagaa gagcgtggtc agtctgaagc cattgcacgc     1500
aacctgcgtg aaatgtctcg cctcggcgta ccggtagttt gtacggttat cggtgaaggt     1560
ggttctggcg gtgcgctggc gattggcgtg ggcgataaag tgaatatgct gcaatacagc     1620
acctattccg ttatctcgcc ggaaggttgt gcgtccattc tgtggaagag cgccgacaaa     1680
gcgccgctgg cggctgaagc gatgggtatc attgctccgc gtctgaaaga actgaaactg     1740
atcgactcca tcatcccgga accactgggt ggtgctcacc gtaacccgga agcgatggcg     1800
gcatcgttga aagcgcaact gctggcggat ctggccgatc tcgacgtgtt aagcactgaa     1860
gatttaaaaa atcgtcgtta tcagcgcctg atgagctacg gttacgcgta agaattcgcc     1920
ttagacatga ctgttcctca gttcaagttg ggcacttacg agaagaccgg tcttgctaga     1980
ttctaatcaa gaggatgtca gaatgccatt tgcctgagag atgcaggctt catttttgat     2040
acttttttat ttgtaaccta tatagtatag gatttttttt gtcatttgt ttcttctcgt      2100 acgagcttgc tcctgatcag cctatctcgc agctgatgaa tatcttgtgg tagggtttg      2160 ggaaaatcat tcgagtttga tgttttttct ggtatttccc actcctcttc agagtacaga     2220
agattaagtg agacgttcgt ttgtgcggat ctaacatcca aagacgaaag gttgaatgaa     2280
acctttttgc catccgacat ccacaggtcc attctcacac ataagtgcca aacgcaacag     2340
gaggggatac actagcagca gaccgttgca aacgcaggac ctccactcct cttctcctca     2400
acacccactt tgccatcga aaaaccagcc cagttattgg gcttgattgg agctcgctca      2460
ttccaattcc ttctattagg ctactaacac catgacttta ttagcctgtc tatcctggcc     2520
cccctggcga ggttcatgtt tgtttatttc cgaatgcaac aagctccgca ttacacccga     2580
acatcactcc agatgagggc tttctgagtg tggggtcaaa tagtttcatg ttccccaaat     2640
ggcccaaaac tgacagttta aacgctgtct tggaacctaa tatgacaaaa gcgtgatctc     2700
atccaagatg aactaagttt ggttcgttga atgctaacg  gccagttggt caaaagaaa      2760 cttccaaaag tcggcatacc gtttgtcttg tttggtattg attgacgaat gctcaaaaat     2820
```

```
aatctcatta atgcttagcg cagtctctct atcgcttctg aacccggtg cacctgtgcc    2880 gaaacgcaaa tggggaaaca cccgcttttt ggatgattat gcattgtctc cacattgtat    2940
gcttccaaga ttctggtggg aatactgctg atagcctaac gttcatgatc aaaatttaac    3000
tgttctaacc cctacttgac agcaatatat aaacagaagg aagctgccct gtcttaaacc    3060
ttttttttta tcatcattat tagcttactt tcataattgc gactggttcc aattgacaag    3120
cttttgattt taacgacttt taacgacaac ttgagaagat caaaaaacaa ctaattattc    3180
gaaacgagga attcaccatg gatattcgta agattaaaaa actgatcgag ctggttgaag    3240
aatcaggcat ctccgaactg gaaatttctg aaggcgaaga gtcagtacgc attagccgtg    3300
cagctcctgc cgcaagtttc cctgtgatgc aacaagctta cgctgcacca atgatgcagc    3360
agccagctca atctaacgca gccgctccgg cgaccgttcc ttccatggaa gcgccagcag    3420
cagcggaaat cagtggtcac atcgtacgtt ccccgatggt tggtactttc taccgcaccc    3480
caagcccgga cgcaaaagcg ttcatcgaag tgggtcagaa agtcaacgtg gcgataccc    3540 tgtgcatcgt tgaagccatg aaaatgatga accagatcga agcggacaaa tccggtaccg    3600
tgaaagcaat tctggtcgaa agtggacaac cggtagaatt tgacgagccg ctggtcgtca    3660
tcgagtaaga attcgcctta gacatgactg ttcctcagtt caagttgggc acttacgaga    3720
agaccggtct gctagattc taatcaagag gatgtcagaa tgccatttgc ctgagagatg    3780
caggcttcat ttttgatact tttttatttg taacctatat agtataggat ttttttttgtc    3840 attttgtttc ttctcgtacg agcttgctcc tgatcagcct atctcgcagc tgatgaatat    3900
cttgtggtag gggtttggga aaatcattcg agtttgatgt ttttcttggt atttcccact    3960
cctcttcaga gtacagaaga ttaagtgaga cgttcgtttg tgcggatcta acatccaaag    4020
acgaaaggtt gaatgaaacc ttttttgccat ccgacatcca caggtccatt ctcacacata    4080
agtgccaaac gcaacaggag gggatacact agcagcagac cgttgcaaac gcaggacctc    4140
cactcctctt ctcctcaaca cccacttttg ccatcgaaaa accagcccag ttattgggct    4200
tgattggagc tcgctcattc caattccttc tattaggcta ctaacaccat gactttatta    4260
gcctgtctat cctggccccc ctggcgaggt tcatgtttgt ttatttccga atgcaacaag    4320
ctccgcatta cacccgaaca tcactccaga tgagggcttt ctgagtgtgg ggtcaaatag    4380
tttcatgttc cccaaatggc ccaaaactga cagtttaaac gctgtcttgg aacctaatat    4440
gacaaaagcg tgatctcatc caagatgaac taagttggt tcgttgaaat gctaacggcc    4500
agttggtcaa aaagaaactt ccaaaagtcg gcataccgtt tgtcttgttt ggtattgatt    4560
gacgaatgct caaaaataat ctcattaatg cttagcgcag tctctctatc gcttctgaac    4620
cccggtgcac ctgtgccgaa acgcaaatgg ggaaacaccc gcttttttgga tgattatgca    4680 ttgtctccac attgtatgct tccaagattc tggtgggaat actgctgata gcctaacgtt    4740
catgatcaaa atttaactgt tctaacccct acttgacagc aatatataaa cagaaggaag    4800
ctgccctgtc ttaaaccttt tttttatca tcattattag cttactttca taattgcgac    4860
tggttccaat tgacaagctt ttgattttaa cgactttaa cgacaacttg agaagatcaa    4920
aaacaactta attattcgaa acgaggaatt caccatgctg gataaaattg ttattgccaa    4980
ccgcggcgag attgcattgc gtattcttcg tgcctgtaaa gaactgggca tcaagactgt    5040
cgctgtgcac tccagcgcgg atcgcgatct aaaacacgta ttactggcag atgaaacggt    5100
ctgtattggc cctgctccgt cagtaaaaag ttatctgaac atcccggcaa tcatcagcgc    5160
cgctgaaatc accggcgcag tagcaatcca tccgggttac ggcttcctct ccgagaacgc    5220
```

```
caactttgcc gagcaggttg aacgctccgg ctttatcttc attggcccga aagcagaaac    5280
cattcgcctg atgggcgaca agtatccgc aatcgcggcg atgaaaaaag cgggcgtccc    5340
ttgcgtaccg ggttctgacg gcccgctggg cgacgatatg gataaaaacc gtgccattgc    5400
taaacgcatt ggttatccgg tgattatcaa agcctccggc ggcggcggcg tcgcggtat    5460
gcgcgtagtg cgcggcgacg ctgaactggc acaatccatc tccatgaccc gtgcggaagc    5520
gaaagctgct ttcagcaacg atatggttta catggagaaa tacctggaaa atcctcgcca    5580
cgtcgagatt caggtactgg ctgacggtca gggcaacgct atctatctgg cggaacgtga    5640
ctgctccatg caacgccgcc accagaaagt ggtcgaagaa gcgccagcac cgggcattac    5700
cccggaactg cgtcgctaca tcggcgaacg ttgcgctaaa gcgtgtgttg atatcggcta    5760
tcgcggtgca ggtactttcg agttcctgtt cgaaaacggc gagttctatt tcatcgaaat    5820
gaacacccgt attcaggtag aacacccggt tacagaaatg atcaccggcg ttgacctgat    5880
caaagaacag ctgcgtatcg ctgccggtca accgctgtcg atcaagcaag aagaagttca    5940
cgttcgcggc catgcggtgg aatgtcgtat caacgccgaa gatccgaaca ccttcctgcc    6000
aagtccgggc aaaatcaccc gtttccacgc acctggcgt tttggcgtac gttgggagtc    6060
tcatatctac gcgggctaca ccgtaccgcc gtactatgac tcaatgatcg gtaagctgat    6120
ttgctacggt gaaaaccgtg acgtggcgat tgcccgcatg aagaatgcgc tgcaggagct    6180
gatcatcgac ggtatcaaaa ccaacgttga tctgcagatc cgcatcatga atgacgagaa    6240
cttccagcat ggtggcacta acatccacta tctggagaaa aaactcggtc ttcaggaaaa    6300
ataagaattc gccttagaca tgactgttcc tcagttcaag ttgggcactt acgagaagac    6360
cggtcttgct agattctaat caagaggatg tcagaatgcc atttgcctga gatgcagg    6420
cttcattttt gatactttt tatttgtaac ctatatagta taggattttt tttgtcattt    6480
tgtttcttct cgtacgagct tgctcctgat cagcctatct cgcagctgat gaatatcttg    6540
tggtaggggt ttgggaaaat cattcgagtt tgatgttttt cttggtattt cccactcctc    6600
ttcagagtac agaagattaa gtgagacgtt cgtttgtgcg gatctaacat ccaaagacga    6660
aaggttgaat gaaaccttt tgccatccga catccacagg tccattctca cacataagtg    6720
ccaaacgcaa caggagggga tacactagca gcagaccgtt gcaaacgcag gacctccact    6780
cctcttctcc tcaacaccca cttttgccat cgaaaaacca gcccagttat tgggcttgat    6840
tggagctcgc tcattccaat tccttctatt aggctactaa caccatgact ttattagcct    6900
gtctatcctg gcccccctgg cgaggttcat gtttgtttat ttccgaatgc aacaagctcc    6960
gcattacacc cgaacatcac tccagatgag ggctttctga gtgtggggtc aaatagtttc    7020
atgttcccca aatggcccaa aactgacagt ttaaacgctg tcttggaacc taatatgaca    7080
aaagcgtgat ctcatccaag atgaactaag tttggttcgt tgaaatgcta acggccagtt    7140
ggtcaaaaag aaacttccaa aagtcggcat accgtttgtc ttgtttggta ttgattgacg    7200
aatgctcaaa aataatctca ttaatgctta gcgcagtctc tctatcgctt ctgaaccccg    7260
gtgcacctgt gccgaaacgc aaatggggaa cacccgctt tttggatgat tatgcattgt    7320
ctccacattg tatgcttcca agattctggt gggaatactg ctgatagcct aacgttcatg    7380
atcaaaattt aactgttcta acccctactt gacagcaata tataaacaga aggaagctgc    7440
cctgtcttaa accttttttt ttatcatcat tattagctta ctttcataat tgcgactggt    7500
tccaattgac aagcttttga ttttaacgac ttttaacgac aacttgagaa gatcaaaaaa    7560
caactaatta ttcgaaacga ggaattgacc atgagctgga ttgaacgaat taaaagcaac    7620
```

```
attactccca cccgcaaggc gagcattcct gaaggggtgt ggactaagtg tgatagctgc    7680
ggtcaggttt tataccgcgc tgagctggaa cgtaatcttg aggtctgtcc gaagtgtgac    7740
catcacatgc gtatgacagc gcgtaatcgc ctgcatagcc tgttagatga aggaagcctt    7800
gtggagctgg gtagcagcgt tgagccgaaa gatgtgctga agtttcgtga ctccaagaag    7860
tataaagacc gtctggcatc tgcgcagaaa gaaaccggcg aaaaagatgc gctggtggtg    7920
atgaaaggca ctctgtatgg aatgccggtt gtcgctgcgg cattcgagtt cgcctttatg    7980
ggcggttcaa tggggtctgt tgtgggtgca cgtttcgtgc gtgccgttga gcaggcgctg    8040
gaagataact gcccgctgat ctgcttctcc gcctctggtg gcgcacgtat gcaggaagca    8100
ctgatgtcgc tgatgcagat ggcgaaaacc tctgcggcac tggcaaaaat gcaggagcgc    8160
ggcttgccgt acatctccgt gctgaccgac ccgacgatgg gcggtgtttc tgcaagtttc    8220
gccatgctgg gcgatctcaa catcgctgaa ccgaaagcgt taatcgcttt gccggtccgc    8280
gtgttatcga acagaaccgt tcgcgaaaaa ctgccgcctg gattccagcg cagtgaattc    8340
ctgatcgaga aggcgcgat cgacatgatc gtccgtcgtc cggaaatgcg cctgaaactg    8400
gcgagcattc tggcgaagtt gatgaatctg ccagcgccga atcctgaagc gccgcgtgaa    8460
ggcgtagtgg tacccccggt accggatcag gaacctgagg cctgataaca attcgcctta    8520
gacatgactg ttcctcagtt caagttgggc acttacgaga agaccggtct tgctagattc    8580
taatcaagag gatgtcagaa tgccatttgc ctgagagatg caggcttcat ttttgatact    8640
ttttattttg taacctatat agtataggat tttttttgtc attttgtttc ttctcgtacg    8700
agcttgctcc tgatcagcct atctcgcagc tgatgaatat cttgtggtag gggtttggga    8760
aaatcattcg agtttgatgt ttttcttggt atttcccact cctcttcaga gtacagaaga    8820
ttaagtgaga cgttcgtttg tgcggatcct aatgcggtag tttatcacag ttaaattgct    8880
aacgcagtca ggcaccgtgt atgaaatcta acaatgcgct catcgtcatc ctcggcaccg    8940
tcaccctgga tgctgtaggc ataggcttgg ttatgccggt actgccgggc ctcttgcggg    9000
atatcgtcca ttccgacagc atcgccagtc actatggcgt gctgctagcg ctatatgcgt    9060
tgatgcaatt tctatgcgca cccgttctcg gagcactgtc cgaccgcttt ggccgccgcc    9120
cagtcctgct cgcttcgcta cttggagcca ctatcgacta cgcgatcatg gcgaccacac    9180
ccgtcctgtg gatctatcga atctaaatgt aagttaaaat ctctaaataa ttaaataagt    9240 cccagttttct ccatacgaac cttaacagca ttgcggtgag catctagacc ttcaacagca    9300
gccagatcca tcactgcttg gccaatatgt ttcagtccct caggagttac gtcttgtgaa    9360
gtgatgaact tctggaaggt tgcagtgtta actccgctgt attgacgggc atatccgtac    9420
gttggcaaag tgtggttggt accggaggag taatctccac aactctctgg agagtaggca    9480
ccaacaaaca cagatccagc gtgttgtact tgatcaacat aagaagaagc attctcgatt    9540
tgcaggatca agtgttcagg agcgtactga ttggacattt ccaaagcctg ctcgtaggtt    9600
gcaaccgata gggttgtaga gtgtgcaata cacttgcgta caatttcaac ccttggcaac    9660
tgcacagctt ggttgtgaac agcatcttca attctggcaa gctccttgtc tgtcatatcg    9720
acagccaaca gaatcacctg gaatcaata ccatgttcag cttgagacag aaggtctgag    9780
gcaacgaaat ctggatcagc gtatttatca gcaataacta gaacttcaga aggcccagca    9840
ggcatgtcaa tactacacag ggctgatgtg tcattttgaa ccatcatctt ggcagcagta    9900
acgaactggt ttcctggacc aaatatttg tcacacttag gaacagtttc tgttccgtaa    9960
gccatagcag ctactgcctg ggcgcctcct gctagcacga tacacttagc accaaccttg    10020
```

```
tgggcaacgt agatgacttc tggggtaagg gtaccatcct tcttaggtgg agatgcaaaa    10080
acaatttctt tgcaaccagc aactttggca ggaacaccca gcatcaggga agtggaaggc    10140
agaattgcgg ttccaccagg aatatagagg ccaactttct caataggtct tgcaaaacga    10200
gagcagacta caccagggca agtctcaact tgcaacgtct ccgttagttg agcttcatgg    10260
aatttcctga cgttatctat agagagatca atggctctct taacgttatc tggcaattgc    10320
ataagttcct ctgggaaagg agcttctaac acaggtgtct caaagcgac tccatcaaac     10380 ttggcagtta gttctaaaag gcttttgtca ccattttgac gaacattgtc gacaattggt    10440
ttgactaatt ccataatctg ttccgttttc tggataggac gacgaagggc atcttcaatt    10500
tcttgtgagg aggccttaga aacgtcaatt ttgcacaatt caatacgacc ttcagaaggg    10560
acttctttag gtttggattc ttctttaggt tgttccttgg tgtatcctgg cttggcatct    10620
cctttccttc tagtgacctt tagggacttc atatccaggt ttctctccac ctcgtccaac    10680
gtcacaccgt acttggcaca tctaactaat gcaaaataaa ataagtcagc acattcccag    10740
gctatatctt ccttggattt agcttctgca agttcatcag cttcctccct aattttagcg    10800
ttcaacaaaa cttcgtcgtc aaataaccgt ttggtataag aaccttctgg agcattgctc    10860
ttacgatccc acaaggtggc ttccatggct ctaagaccct ttgattggcc aaaacaggaa    10920
gtgcgttcca agtgacagaa accaacacct gtttgttcaa ccacaaattt caagcagtct    10980
ccatcacaat ccaattcgat acccagcaac ttttgagttg ctccagatgt agcaccttta    11040
taccacaaac cgtgacgacg agattggtag actccagttt gtgtccttat agcctccgga    11100
atagactttt tggacgagta caccaggccc aacgagtaat tagaagagtc agccaccaaa    11160
gtagtgaata gaccatcggg gcggtcagta gtcaaagacg ccaacaaaat ttcactgaca    11220
gggaactttt tgacatcttc agaaagttcg tattcagtag tcaattgccg agcatcaata    11280
atggggatta taccagaagc aacagtggaa gtcacatcta ccaactttgc ggtctcagaa    11340
aaagcataaa cagttctact accgccatta gtgaaacttt tcaaatcgcc cagtggagaa    11400
gaaaaaggca cagcgatact agcattagcg ggcaaggatg caactttatc aaccagggtc    11460
ctatagataa ccctagcgcc tgggatcatc ctttggacaa ctctttctgc caaatctagg    11520
tccaaaatca cttcattgat accattattg tacaacttga gcaagttgtc gatcagctcc    11580
tcaaattggt cctctgtaac ggatgactca acttgcacat taacttgaag ctcagtcgat    11640
tgagtgaact tgatcaggtt gtgcagctgg tcagcagcat agggaaacac ggcttttcct    11700
accaaactca aggaattatc aaactctgca acacttgcgt atgcaggtag caaggaaat    11760 gtcatacttg aagtcggaca gtgagtgtag tcttgagaaa ttctgaagcc gtatttttat    11820
tatcagtgag tcagtcatca ggagatcctc tacgccggac gcatcgtggc cggcatcacc    11880
ggcgccacag gtgcggttgc tggcgcctat atcgccgaca tcaccgatgg ggaagatcgg    11940
gctcgccact tcgggctcat gagcgcttgt ttcgcgtgg gtatggtggc aggccccgtg     12000
gccgggggac tgttgggcgc catctccttg catgcaccat tccttgcggc ggcggtgctc    12060
aacggcctca acctactact gggctgcttc ctaatgcagg agtcgcataa gggagagcgt    12120
cgagtatcta tgattggaag tatgggaatg gtgatacccg cattcttcag tgtcttgagg    12180
tctcctatca gattatgccc aactaaagca accggaggag gagatttcat ggtaaatttc    12240
tctgactttt ggtcatcagt agactcgaac tgtgagacta tctcggttat gacagcagaa    12300
atgtccttct tggagacagt aaatgaagtc ccaccaataa gaaatccctt gttatcagga    12360
acaaacttct tgtttcgaac ttttcggtg ccttgaacta taaaatgtag agtggatatg     12420
```

```
tcgggtagga atggagcggg caaatgctta ccttctggac cttcaagagg tatgtagggt   12480
ttgtagatac tgatgccaac ttcagtgaca acgttgctat ttcgttcaaa ccattccgaa   12540
tccagagaaa tcaaagttgt ttgtctacta ttgatccaag ccagtgcggt cttgaaactg   12600
acaatagtgt gctcgtgttt tgaggtcatc tttgtatgaa taaatctagt ctttgatcta   12660
aataatcttg acgagccaag gcgataaata cccaaatcta aaactctttt aaaacgttaa   12720
aaggacaagt atgtctgcct gtattaaacc ccaaatcagc tcgtagtctg atcctcatca   12780
acttgagggg cactatcttg ttttagagaa atttgcggag atgcgatatc gagaaaaagg   12840
tacgctgatt ttaaacgtga aatttatctc aagatctgct gcctcgcgcg tttcggtgat   12900
gacggtgaaa acctctgaca catgcagctc ccggagacgg tcacagcttg tctgtaagcg   12960
gatgccggga gcagacaagc ccgtcagggc gcgtcagcgg gtgttggcgg gtgtcggggc   13020
gcagccatga cccagtcacg tagcgatagc ggagtgtata ctggcttaac tatgcggcat   13080
cagagcagat tgtactgaga gtgcaccata tgcggtgtga ataccgcac agatgcgtaa    13140
ggagaaaata ccgcatcagg cgctcttccg cttcctcgct cactgactcg ctgcgctcgg   13200
tcgttcggct gcggcgagcg gtatcagctc actcaaaggc ggtaatacgg ttatccacag   13260
aatcagggga taacgcagga agaacatgt gagcaaaagg ccagcaaaag gccaggaacc    13320
gtaaaaaggc cgcgttgctg gcgtttttcc ataggctccg ccccctgac gagcatcaca    13380
aaaatcgacg ctcaagtcag aggtggcgaa acccgacagg actataaaga taccaggcgt   13440
ttccccctgg aagctccctc gtgcgctctc ctgttccgac cctgccgctt accggatacc   13500
tgtccgcctt tctcccttcg ggaagcgtgg cgctttctca atgctcacgc tgtaggtatc   13560
tcagttcggt gtaggtcgtt cgctccaagc tgggctgtgt gcacgaaccc cccgttcagc   13620
ccgaccgctg cgccttatcc ggtaactatc gtcttgagtc aacccggta agacacgact    13680
tatcgccact ggcagcagcc actggtaaca ggattagcag agcgaggtat gtaggcggtg   13740
ctacagagtt cttgaagtgg tggcctaact acggctacac tagaaggaca gtatttggta   13800
tctgcgctct gctgaagcca gttaccttcg gaaaaagagt tggtagctct tgatccggca   13860
aacaaaccac cgctggtagc ggtggttttt ttgtttgcaa gcagcagatt acgcgcagaa   13920
aaaaaggatc tcaagaagat cctttgatct tttctacggg gtctgacgct cagtggaacg   13980
aaaactcacg ttaagggatt ttggtcatga gattatcaaa aaggatcttc acctagatcc   14040
ttttaaatta aaaatgaagt tttaaatcaa tctaaagtat atatgagtaa acttggtctg   14100
acagttacca atgcttaatc agtgaggcac ctatctcagc gatctgtcta tttcgttcat   14160
ccatagttgc ctgactcccc gtcgtgtaga taactacgat acgggagggc ttaccatctg   14220
gccccagtgc tgcaatgata ccgcgagacc cacgctcacc ggctccagat ttatcagcaa   14280
taaaccagcc agccggaagg gccgagcgca gaagtggtcc tgcaacttta tccgcctcca   14340
tccagtctat taattgttgc cgggaagcta gagtaagtag ttcgccagtt aatagtttgc   14400
gcaacgttgt tgccattgct gcaggcatcg tggtgtcacg ctcgtcgttt ggtatggctt   14460
cattcagctc cggttcccaa cgatcaaggc gagttacatg atccccatg ttgtgcaaaa    14520
aagcggttag ctccttcggt cctccgatcg ttgtcagaag taagttggcc gcagtgttat   14580
cactcatggt tatggcagca ctgcataatt ctcttactgt catgccatcc gtaagatgct   14640
tttctgtgac tggtgagtac tcaaccaagt cattctgaga atagtgtatg cggcgaccga   14700
gttgctcttg cccggcgtca acacgggata ataccgcgcc acatagcaga actttaaaag   14760
tgctcatcat tggaaaacgt tcttcggggc gaaaactctc aaggatctta ccgctgttga   14820
```

| | | |
|---|---|---|
| gatccagttc gatgtaaccc actcgtgcac ccaactgatc ttcagcatct tttactttca | 14880 |
| ccagcgtttc tgggtgagca aaaacaggaa ggcaaaatgc cgcaaaaaag ggaataaggg | 14940 |
| cgacacggaa atgttgaata ctcatactct tccttttca atattattga agcatttatc | 15000 |
| agggttattg tctcatgagc ggatacatat ttgaatgtat ttagaaaaat aaacaaatag | 15060 |
| gggttccgcg cacatttccc cgaaaagtgc cacctgacgt ctaagaaacc attattatca | 15120 |
| tgacattaac ctataaaaat aggcgtatca cgaggccctt tcgtcttcaa gaattaattc | 15180 |
| tcatgtttga cagcttatca tcgataagct gactcatgtt ggtattgtga aatagacgca | 15240 |
| gatcgggaac actgaaaaat aacagttatt attcg | 15275 |

<210> SEQ ID NO 7
<211> LENGTH: 9484
<212> TYPE: DNA
<213> ORGANISM: Artificial
<220> FEATURE:
<223> OTHER INFORMATION: Chemically Synthesized

<400> SEQUENCE: 7

| | | |
|---|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggcccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcgcca taccgttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga acacccgct | 660 |
| tttggatga ttatgcattg tctccacatt gtatgcttcc aagattctgg tgggaatact | 720 |
| gctgatagcc taacgttcat gatcaaaatt taactgttct aaccccctact tgacagcaat | 780 |
| atataaacag aaggaagctg ccctgtctta aaccttttt tttatcatca ttattagctt | 840 |
| actttcataa ttgcgactgg ttccaattga caagcttttg attttaacga cttttaacga | 900 |
| caacttgaga agatcaaaaa acaactaatt attcgaagga tcctacgtag aattcaccat | 960 |
| ggatattcgt aagattaaaa actgatcga gctggttgaa gaatcaggca tctccgaact | 1020 |
| ggaaatttct gaaggcgaag agtcagtacg cattagccgt gcagctcctg ccgcaagttt | 1080 |
| ccctgtgatg caacaagctt acgctgcacc aatgatgcag cagccagctc aatctaacgc | 1140 |
| agccgctccg gcgaccgttc cttccatgga agcgccagca gcagcggaaa tcagtggtca | 1200 |
| catcgtacgt tccccgatgg ttggtacttt ctaccgcacc ccaagcccgg acgcaaaagc | 1260 |
| gttcatcgaa gtgggtcaga agtcaacgt gggcgatacc ctgtgcatcg ttgaagccat | 1320 |
| gaaaatgatg aaccagatcg aagcggacaa atccggtacc gtgaaagcaa ttctggtcga | 1380 |
| aagtggacaa ccggtagaat tgacgagcc gctggtcgtc atcgagtaag aattccctag | 1440 |
| ggcggccgcg aattaattcg ccttagacat gactgttcct cagttcaagt tgggcactta | 1500 |
| cgagaagacc ggtcttgcta gattctaatc aagaggatgt cagaatgcca tttgcctgag | 1560 |
| agatgcaggc ttcattttg atacttttt atttgtaacc tatatagtat aggatttttt | 1620 |

```
ttgtcatttt gtttcttctc gtacgagctt gctcctgatc agcctatctc gcagctgatg    1680
aatatcttgt ggtaggggtt tgggaaaatc attcgagttt gatgtttttc ttggtatttc    1740
ccactcctct tcagagtaca gaagattaag tgagaagttc gtttgtgcaa gcttatcgat    1800
aagctttaat gcggtagttt atcacagtta aattgctaac gcagtcaggc accgtgtatg    1860
aaatctaaca atgcgctcat cgtcatcctc ggcaccgtca ccctggatgc tgtaggcata    1920
ggcttggtta tgccggtact gccgggcctc ttgcgggata tcgtccattc cgacagcatc    1980
gccagtcact atggcgtgct gctagcgcta tatgcgttga tgcaatttct atgcgcaccc    2040
gttctcggag cactgtccga ccgctttggc cgccgcccag tcctgctcgc ttcgctactt    2100
ggagccacta tcgactacgc gatcatggcg accacacccg tcctgtggat ctatcgaatc    2160
taaatgtaag ttaaaatctc taaataatta ataagtccc  agtttctcca tacgaacctt    2220
aacagcattg cggtgagcat ctagaccttc aacagcagcc agatccatca ctgcttggcc    2280
aatatgtttc agtccctcag gagttacgtc ttgtgaagtg atgaacttct ggaaggttgc    2340
agtgttaact ccgctgtatt gacgggcata tccgtacgtt ggcaaagtgt ggttggtacc    2400
ggaggagtaa tctccacaac tctctggaga gtaggcacca caaacacag  atccagcgtg    2460 ttgtacttga tcaacataag aagaagcatt ctcgatttgc aggatcaagt gttcaggagc    2520
gtactgattg gacatttcca aagcctgctc gtaggttgca accgataggg ttgtagagtg    2580
tgcaatacac ttgcgtacaa tttcaaccct tggcaactgc acagcttggt tgtgaacagc    2640
atcttcaatt ctggcaagct ccttgtctgt catatcgaca gccaacagaa tcacctggga    2700
atcaatacca tgttcagctt gagacagaag gtctgaggca acgaaatctg gatcagcgta    2760
tttatcagca ataactagaa cttcagaagg cccagcaggc atgtcaatac tacacagggc    2820
tgatgtgtca ttttgaacca tcatcttggc agcagtaacg aactggtttc ctggaccaaa    2880
tattttgtca cacttaggaa cagtttctgt tccgtaagcc atagcagcta ctgcctgggc    2940
gcctcctgct agcacgatac acttagcacc aaccttgtgg gcaacgtaga tgacttctgg    3000
ggtaagggta ccatccttct taggtggaga tgcaaaaaca atttctttgc aaccagcaac    3060
tttggcagga acacccagca tcagggaagt ggaaggcaga attgcggttc caccaggaat    3120
atagaggcca actttctcaa taggtcttgc aaaacgagag cagactacac cagggcaagt    3180
ctcaacttgc aacgtctccg ttagttgagc ttcatggaat ttcctgacgt tatctataga    3240
gagatcaatg gctctcttaa cgttatctgg caattgcata agttcctctg gaaaggagc    3300 ttctaacaca ggtgtcttca aagcgactcc atcaaacttg gcagttagtt ctaaaagggc    3360
tttgtcacca ttttgacgaa cattgtcgac aattggtttg actaattcca taatctgttc    3420
cgttttctgg ataggacgac gaagggcatc ttcaatttct tgtgaggagg ccttagaaac    3480
gtcaattttg cacaattcaa tacgaccttc agaagggact tctttaggtt tggattcttc    3540
tttaggttgt tccttggtgt atcctggctt ggcatctcct ttccttctag tgacctttag    3600
ggacttcata tccaggtttc tctccacctc gtccaacgtc acccgtact  tggcacatct    3660 aactaatgca aaataaaata agtcagcaca ttcccaggct atatcttcct tggatttagc    3720
ttctgcaagt tcatcagctt cctccctaat tttagcgttc aacaaaactt cgtcgtcaaa    3780
taaccgtttg gtataagaac cttctggagc attgctctta cgatcccaca aggtggcttc    3840
catggctcta agaccctttg attggccaaa acaggaagtg cgttccaagt gacagaaacc    3900
aacacctgtt tgttcaacca caaatttcaa gcagtctcca tcacaatcca attcgatacc    3960
cagcaacttt tgagttgctc cagatgtagc acctttatac cacaaaccgt gacgacgaga    4020
```

```
ttggtagact ccagtttgtg tccttatagc ctccggaata gacttttggg acgagtacac   4080
caggcccaac gagtaattag aagagtcagc caccaaagta gtgaatagac catcggggcg   4140
gtcagtagtc aaagacgcca acaaaatttc actgacaggg aacttttga catcttcaga    4200 aagttcgtat tcagtagtca attgccgagc atcaataatg gggattatac cagaagcaac   4260
agtggaagtc acatctacca actttgcggt ctcagaaaaa gcataaacag ttctactacc   4320
gccattagtg aaacttttca aatcgcccag tggagaagaa aaaggcacag cgatactagc   4380
attagcgggc aaggatgcaa ctttatcaac cagggtccta tagataaccc tagcgcctgg   4440
gatcatcctt tggacaactc tttctgccaa atctaggtcc aaaatcactt cattgatacc   4500
attattgtac aacttgagca agttgtcgat cagctcctca aattggtcct ctgtaacgga   4560
tgactcaact tgcacattaa cttgaagctc agtcgattga gtgaacttga tcaggttgtg   4620
cagctggtca gcagcatagg gaaacacggc ttttcctacc aaactcaagg aattatcaaa   4680
ctctgcaaca cttgcgtatg caggtagcaa gggaaatgtc atacttgaag tcggacagtg   4740
agtgtagtct tgagaaattc tgaagccgta tttttattat cagtgagtca gtcatcagga   4800
gatcctctac gccggacgca tcgtggccga cctgcagggg ggggggggc gctgaggtct   4860 gcctcgtgaa gaaggtgttg ctgactcata ccaggcctga atcgcccat catccagcca    4920 gaaagtgagg gagccacggt tgatgagagc tttgttgtag gtggaccagt tggtgatttt   4980
gaacttttgc tttgccacgg aacggtctgc gttgtcggga agatgcgtga tctgatcctt   5040
caactcagca aaagttcgat ttattcaaca aagccgccgt cccgtcaagt cagcgtaatg   5100
ctctgccagt gttacaacca attaaccaat tctgattaga aaactcatc gagcatcaaa    5160 tgaaactgca atttattcat atcaggatta tcaataccat attttgaaa agccgtttc     5220 tgtaatgaag gagaaaactc accgaggcag ttccatagga tggcaagatc ctggtatcgg   5280
tctgcgattc cgactcgtcc aacatcaata caacctatta atttcccctc gtcaaaaata   5340
aggttatcaa gtgagaaatc accatgagtg acgactgaat ccggtgagaa tggcaaaagc   5400
ttatgcattt ctttccagac ttgttcaaca ggccagccat tacgctcgtc atcaaaatca   5460
ctcgcatcaa ccaaaccgtt attcattcgt gattgcgcct gagcgagacg aaatacgcga   5520
tcgctgttaa aaggacaatt acaaacagga atcgaatgca accggcgcag gaacactgcc   5580
agcgcatcaa caatatttc acctgaatca ggatattctt ctaatacctg gaatgctgtt    5640
ttcccgggga tcgcagtggt gagtaaccat gcatcatcag gagtacggat aaaatgcttg   5700
atggtcggaa gaggcataaa ttccgtcagc cagtttagtc tgaccatctc atctgtaaca   5760
tcattggcaa cgctaccttt gccatgtttc agaaacaact ctggcgcatc gggcttccca   5820
tacaatcgat agattgtcgc acctgattgc ccgacattat cgcgagccca tttataccca   5880
tataaatcag catccatgtt ggaatttaat cgcggcctcg agcaagacgt ttcccgttga   5940
atatggctca taacacccct tgtattactg tttatgtaag cagacagttt tattgttcat   6000
gatgatatat ttttatcttg tgcaatgtaa catcagagat tttgacacac aacgtggctt   6060 tcccccccc ccctgcaggt cggcatcacc ggcgccacag gtgcggttgc tggcgcctat    6120
atcgccgaca tcaccgatgg ggaagatcgg gctcgccact tcgggctcat gagcgcttgt   6180
ttcggcgtgg gtatggtggc aggccccgtg gccggggac tgttgggcgc catctccttg    6240
catgcaccat tccttgcggc ggcggtgctc aacggcctca acctactact gggctgcttc   6300
ctaatgcagg agtcgcataa gggagagcgt cgagtatcta tgattggaag tatgggaatg   6360
gtgatacccg cattcttcag tgtcttgagg tctcctatca gattatgccc aactaaagca   6420
```

```
accggaggag gagatttcat ggtaaatttc tctgactttt ggtcatcagt agactcgaac   6480
tgtgagacta tctcggttat gacagcagaa atgtccttct tggagacagt aaatgaagtc   6540
ccaccaataa agaaatcctt gttatcagga acaaacttct tgtttcgaac tttttcggtg   6600
ccttgaacta taaaatgtag agtggatatg tcgggtagga atggagcggg caaatgctta   6660
ccttctggac cttcaagagg tatgtagggt ttgtagatac tgatgccaac ttcagtgaca   6720
acgttgctat ttcgttcaaa ccattccgaa tccagagaaa tcaaagttgt ttgtctacta   6780
ttgatccaag ccagtgcggt cttgaaactg acaatagtgt gctcgtgttt tgaggtcatc   6840
tttgtatgaa taaatctagt ctttgatcta aataatcttg acgagccaag gcgataaata   6900
cccaaatcta aaactctttt aaaacgttaa aggacaagt atgtctgcct gtattaaacc   6960
ccaaatcagc tcgtagtctg atcctcatca acttgagggg cactatcttg ttttagagaa   7020
atttgcggag atgcgatatc gagaaaaagg tacgctgatt ttaaacgtga aatttatctc   7080
aagatctctg cctcgcgcgt ttcggtgatg acggtgaaaa cctctgacac atgcagctcc   7140
cggagacggt cacagcttgt ctgtaagcgg atgccgggag cagacaagcc cgtcagggcg   7200
cgtcagcggg tgttggcggg tgtcggggcg cagccatgac ccagtcacgt agcgatagcg   7260
gagtgtatac tggcttaact atgcggcatc agagcagatt gtactgagag tgcaccatat   7320
gcggtgtgaa ataccgcaca gatgcgtaag gagaaaatac cgcatcaggc gctcttccgc   7380
ttcctcgctc actgactcgc tgcgctcggt cgttcggctg cggcgagcgg tatcagctca   7440
ctcaaaggcg gtaatacggt tatccacaga atcaggggat aacgcaggaa agaacatgtg   7500
agcaaaaggc cagcaaaagg ccaggaaccg taaaaaggcc gcgttgctgg cgttttttcca   7560 taggctccgc cccctgacg agcatcacaa aaatcgacgc tcaagtcaga ggtggcgaaa   7620
cccgacagga ctataaagat accaggcgtt tccccctgga agctccctcg tgcgctctcc   7680
tgttccgacc ctgccgctta ccggatacct gtccgccttt ctcccttcgg gaagcgtggc   7740
gctttctcaa tgctcacgct gtaggtatct cagttcggtg taggtcgttc gctccaagct   7800
gggctgtgtg cacgaacccc ccgttcagcc cgaccgctgc gccttatccg gtaactatcg   7860
tcttgagtcc aacccggtaa gacacgactt atcgccactg gcagcagcca ctggtaacag   7920
gattagcaga gcgaggtatg taggcggtgc tacagagttc ttgaagtggt ggcctaacta   7980
cggctacact agaaggacag tatttggtat ctgcgctctg ctgaagccag ttaccttcgg   8040
aaaaagagtt ggtagctctt gatccggcaa acaaaccacc gctggtagcg gtggtttttt   8100
tgtttgcaag cagcagatta cgcgcagaaa aaaaggatct caagaagatc ctttgatctt   8160
ttctacgggg tctgacgctc agtggaacga aaactcacgt taagggattt tggtcatgag   8220
attatcaaaa aggatcttca cctagatcct tttaaattaa aaatgaagtt ttaaatcaat   8280
ctaaagtata tatgagtaaa cttggtctga cagttaccaa tgcttaatca gtgaggcacc   8340
tatctcagcg atctgtctat ttcgttcatc catagttgcc tgactccccg tcgtgtagat   8400
aactacgata cgggagggct taccatctgg ccccagtgct gcaatgatac cgcgagaccc   8460
acgctcaccg gctccagatt tatcagcaat aaaccagcca gccggaaggg ccgagcgcag   8520
aagtggtcct gcaactttat ccgcctccat ccagtctatt aattgttgcc gggaagctag   8580
agtaagtagt tcgccagtta atagtttgcg caacgttgtt gccattgctg caggcatcgt   8640
ggtgtcacgc tcgtcgtttg gtatggcttc attcagctcc ggttcccaac gatcaaggcg   8700
agttacatga tcccccatgt tgtgcaaaaa agcggttagc tccttcggtc ctccgatcgt   8760
tgtcagaagt aagttggccg cagtgttatc actcatggtt atggcagcac tgcataattc   8820
```

-continued

```
tcttactgtc atgccatccg taagatgctt ttctgtgact ggtgagtact caaccaagtc    8880
attctgagaa tagtgtatgc ggcgaccgag ttgctcttgc ccggcgtcaa cacgggataa    8940
taccgcgcca catagcagaa ctttaaaagt gctcatcatt ggaaaacgtt cttcggggcg    9000
aaaactctca aggatcttac cgctgttgag atccagttcg atgtaaccca ctcgtgcacc    9060
caactgatct tcagcatctt ttactttcac cagcgtttct gggtgagcaa aaacaggaag    9120
gcaaaatgcc gcaaaaaagg gaataagggc gacacggaaa tgttgaatac tcatactctt    9180 ccttttcaa tattattgaa gcatttatca gggttattgt ctcatgagcg gatacatatt     9240
tgaatgtatt tagaaaaata aacaaatagg ggttccgcgc acatttcccc gaaaagtgcc    9300
acctgacgtc taagaaacca ttattatcat gacattaacc tataaaaata ggcgtatcac    9360
gaggcccttt cgtcttcaag aattaattct catgtttgac agcttatcat cgataagctg    9420
actcatgttg gtattgtgaa atagacgcag atcgggaaca ctgaaaaata acagttatta    9480
ttcg                                                                 9484

<210> SEQ ID NO 8
<211> LENGTH: 37
<212> TYPE: DNA
<213> ORGANISM: Escherichia coli

<400> SEQUENCE: 8
gactaatacg aattcaccat gagtctgaat ttccttg                             37

<210> SEQ ID NO 9
<211> LENGTH: 34
<212> TYPE: DNA
<213> ORGANISM: Escherichia coli

<400> SEQUENCE: 9
cagaactttg aattcttacg cgtaaccgta gctc                                34

<210> SEQ ID NO 10
<211> LENGTH: 36
<212> TYPE: DNA
<213> ORGANISM: Escherichia coli

<400> SEQUENCE: 10
agagtacggg aattcaccat ggatattcgt aagatt                              36

<210> SEQ ID NO 11
<211> LENGTH: 33
<212> TYPE: DNA
<213> ORGANISM: Escherichia coli

<400> SEQUENCE: 11
agcatgttcg aattcttact cgatgacgac cag                                 33

<210> SEQ ID NO 12
<211> LENGTH: 36
<212> TYPE: DNA
<213> ORGANISM: Escherichia coli

<400> SEQUENCE: 12
tcgagtaacg aattcaccat gctggataaa attgtt                              36

<210> SEQ ID NO 13
<211> LENGTH: 33
<212> TYPE: DNA
<213> ORGANISM: Escherichia coli
```

```
<400> SEQUENCE: 13
gacgctttag aattcttatt tttcctgaag acc                                 33

<210> SEQ ID NO 14
<211> LENGTH: 35
<212> TYPE: DNA
<213> ORGANISM: Escherichia coli

<400> SEQUENCE: 14
cagacagaac aattgaccat gagctggatt gaacg                               35

<210> SEQ ID NO 15
<211> LENGTH: 33
<212> TYPE: DNA
<213> ORGANISM: Escherichia coli

<400> SEQUENCE: 15
ccctgccctc aattgttatc aggcctcagg ttc                                 33
```